United States Patent
Stephanou

(10) Patent No.: US 10,458,940 B1
(45) Date of Patent: Oct. 29, 2019

(54) NON-DESTRUCTIVE INSTRUMENT FOR DETECTING POLYMER INSERTS WITHIN POLYMER PIPES FITTED WITH A LOCATOR WIRE

(71) Applicant: Atlas Sensors, LLC, Sunnyvale, CA (US)

(72) Inventor: Philip J. Stephanou, Mountain View, CA (US)

(73) Assignee: Atlas Sensors, LLC, Mountain View, CA (US)

( * ) Notice: Subject to any disclaimer, the term of this patent is extended or adjusted under 35 U.S.C. 154(b) by 29 days.

(21) Appl. No.: 15/191,446

(22) Filed: Jun. 23, 2016

Related U.S. Application Data

(60) Provisional application No. 62/184,263, filed on Jun. 25, 2015, provisional application No. 62/258,538, filed on Nov. 23, 2015, provisional application No. 62/266,722, filed on Dec. 14, 2015.

(51) Int. Cl.
*G01N 27/22* (2006.01)
*G01R 27/26* (2006.01)

(52) U.S. Cl.
CPC ....... *G01N 27/228* (2013.01); *G01R 27/2605* (2013.01)

(58) Field of Classification Search
CPC .......................... G01N 27/228; G01R 27/2605
USPC .................................................. 324/658–690
See application file for complete search history.

(56) References Cited

U.S. PATENT DOCUMENTS

| | | | | |
|---|---|---|---|---|
| 4,752,727 A | * | 6/1988 | Schneider | G01F 1/712 324/178 |
| 5,468,091 A | * | 11/1995 | Arnold | F16L 55/164 405/157 |
| 6,693,444 B2 | * | 2/2004 | Lin | G01N 27/02 324/664 |
| 7,839,282 B1 | * | 11/2010 | Mathur | G01D 5/2405 324/519 |
| 2004/0237632 A1 | * | 12/2004 | Van Keeken | F16L 23/003 73/46 |
| 2005/0104600 A1 | * | 5/2005 | Cotton | B08B 9/049 324/519 |
| 2012/0074953 A1 | * | 3/2012 | Stickelmann | G01R 19/16538 324/537 |
| 2015/0355126 A1 | * | 12/2015 | Voutilainen | G01N 27/24 324/671 |
| 2016/0047369 A1 | * | 2/2016 | Wood | F04B 15/02 417/53 |

FOREIGN PATENT DOCUMENTS

WO  WO 2014/118425  *  2/2013  ............. G01N 27/22

* cited by examiner

*Primary Examiner* — Jeff W Natalini
(74) *Attorney, Agent, or Firm* — Van Pelt, Yi & James LLP

(57) ABSTRACT

A system for insert detection includes a sensor and a processor. The processor is configured to receive capacitance measurement associated with the sensor and determine presence or absence of an insert based at least in part on the capacitance measurement and a threshold.

19 Claims, 23 Drawing Sheets

Section A-A

Section B-B

Section C-C

NON-DESTRUCTIVE INSTRUMENT FOR DETECTING POLYMER INSERTS WITHIN POLYMER PIPES FITTED WITH A LOCATOR WIRE

This application claims priority to U.S. Provisional Patent Application No. 62/184,263 entitled NON-DESTRUCTIVE INSTRUMENT FOR DETECTING INSERTS WITHIN NON-METALLIC PIPES filed Jun. 25, 2015 which is incorporated herein by reference for all purposes; U.S. Provisional Patent Application No. 62/258,538 entitled NON-DESTRUCTIVE INSTRUMENT FOR DETECTING INSERTS WITHIN NON-METALLIC PIPES FITTED WITH A TRACER WIRE filed Nov. 23, 2015 which is incorporated herein by reference for all purposes; and U.S. Provisional Patent Application No. 62/266,722 entitled NON-DESTRUCTIVE INSTRUMENT FOR DETECTING POLYMER INSERTS WITHIN POLYMER PIPES FITTED WITH TRACER WIRE filed Dec. 14, 2015 which is incorporated herein by reference for all purposes.

BACKGROUND

Non-metallic pipes are widely used for transporting low pressure gases. For example, Medium Density Poly-Ethylene (MDPE), High Density Poly-Ethylene (HDPE), and Aldyl-A pipes are used in natural gas distribution networks that transport natural gas from high pressure transmission pipelines to end users. The practice of nesting pipe inserts within previously installed lengths of "parent" or "host" pipeline is used as a lower cost alternative to removing and replacing existing distribution pipeline sections that have become unfit for service (e.g., because of aging or accidentally inflicted damage). Additionally, it is customary to fit a locator or tracer wire along the length of the parent pipe to facilitate locating the otherwise non-conductive pipe using a metal detector while the pipe is buried in the ground. Safely working on distribution pipeline requires a-priori knowledge of the presence or absence of such inserts, which must be gleaned without damaging the pipe or disrupting the flow of gas within. Existing approaches based on, for example, radiography or tapping into the line require expensive equipment, service disruptions, highly trained operators, and special safety precautions.

BRIEF DESCRIPTION OF THE DRAWINGS

Various embodiments of the invention are disclosed in the following detailed description and the accompanying drawings.

DETAILED DESCRIPTION

Figure 1:
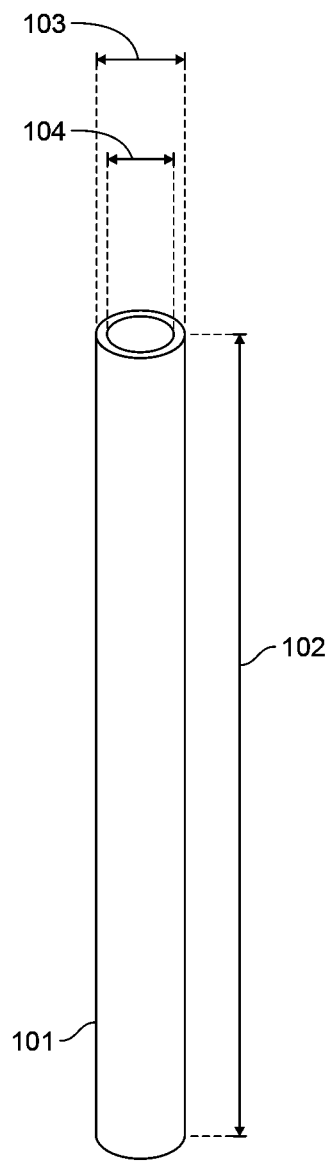
FIG. 1 is a schematic diagram illustrating an embodiment of a length of pipe.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term "processor" refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

A system for insert detection is disclosed. The system comprises a sensor and a processor. The processor is configured to receive capacitance measurement associated with the sensor and determine presence or absence of an insert based at least in part on the capacitance measurement and a threshold.

In some embodiments, a pipe detection instrument is disclosed. In some embodiments, a system for determining the presence or absence of a pipe insert within a non-metallic parent pipe that may be fitted with a tracer wire is disclosed. The system comprises a sensor and a processor. The sensor is for measuring a set of voltage or current responses corresponding to a set of electrostatic excitations. The set of voltage or current responses includes measurements to enable determination of an impedance or capacitance for each of the set of electrostatic excitations. The set of electrostatic excitations may include electrostatic excitations at a plurality of frequencies. The processor is for determining the presence or absence of a pipe insert within a non-metallic parent pipe using the impedance or capacitance determined from each of the set of voltage or current responses corresponding to each of the set of electrostatic excitations.

In some embodiments, a method for determining the presence or absence of a pipe insert (or "carrier") within a non-metallic parent (or "host") pipe comprises receiving a set of voltage or current responses corresponding to a set of electrostatic excitations. The presence or absence of a pipe insert is determined using measurements of a voltage or current response to determine a corresponding impedance or capacitance response for each of the set of electrostatic excitations. For example, an indication is provided to generate an electrostatic excitation at an amplitude and a frequency and a signal is received that is detected to measure a voltage or current response. The excitation may be applied to the outer periphery of a non-metallic pipe such that the resulting electrostatic fields interact with the pipe walls and material within. Accordingly, the voltage or current response is affected by the dielectric properties of the pipe wall and its contents. The frequency may be set to a plurality of frequencies at the same amplitude and, at each frequency of the set of frequencies, the response is received. This produces a set of voltage or current responses corresponding to a set of electrostatic excitations. In some embodiments, a voltage response may be translated into a corresponding current response using a voltage-to-current converter (e.g., a resistor or transimpedance amplifier). An impedance and/or capacitance is determined for each voltage response or current in the set of voltage responses. The presence or absence of a pipe insert is determined using the capacitance values. In various embodiments, a shielded enclosure may isolate an electrostatic excitation generated within the sensor and the resulting voltage or current response from external electromagnetic interference (EMI). In various embodiments, a shielded enclosure may isolate an electrostatic excitation generated within the sensor and the resulting voltage or current response from EMI from a tracer (or "locator") wire fitted to a pipe. In various embodiments, the presence or absence of a pipe insert within a parent pipe is determined using capacitance values measured at multiple orientations around the parent pipe.

Target Samples

In some embodiments, a device for determining the presence or absence of a pipe insert within a non-metallic parent pipe (e.g., a segment of Medium Density Poly-Ethylene natural gas distribution pipeline or poly-vinyl chloride service conduit) is disclosed. The device determines the presence or absence of an insert within a specimen based on transducing electrostatic fields within the sample and correlating the resulting voltage or current response to a capacitance value that is indicative of the dielectric response of either a pipe not containing an insert or of a pipe containing an insert. In various embodiments, the device includes one or more electrodes, a shield, an enclosure, power electronics, signal processors, a memory, a user interface, or any other appropriate device component.

FIG. 1 is a schematic diagram illustrating an embodiment of a length of pipe. In the example shown, pipe 101 has length 102, outer diameter 103, and inner diameter 104.

Figure 2:
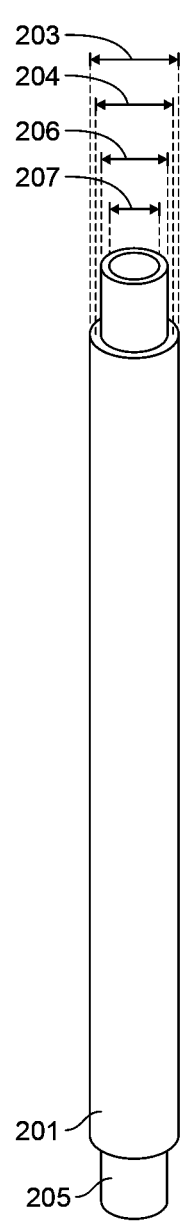
FIG. 2 is a schematic diagram illustrating an embodiment of a length of parent pipe containing a pipe insert.

FIG. 2 is a schematic diagram illustrating an embodiment of a length of parent pipe containing a pipe insert. In the example shown, parent or host pipe 201 has outer diameter 203 and inner diameter 204, and insert or carrier 205 has outer diameter 206 and inner diameter 207. Outer diameter 206 is less than inner diameter 204 such that insert 205 can be inserted within pipe 201.

Figure 3:
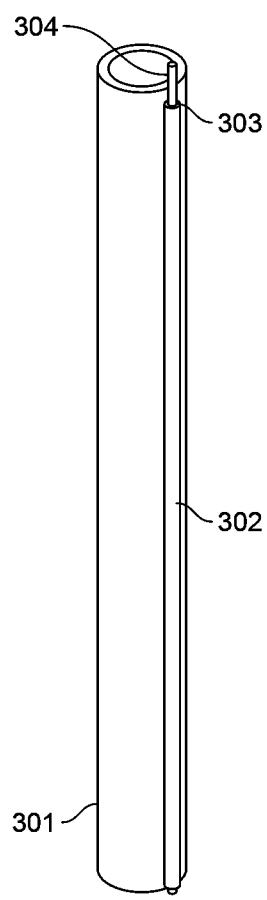
FIG. 3 is a schematic diagram illustrating an embodiment of a length of pipe fitted with a length of tracer or locator wire.

FIG. 3 is a schematic diagram illustrating an embodiment of a length of pipe fitted with a length of tracer or locator wire. In the example shown, tracer wire 302 has conductor 304 surrounded by dielectric insulation 303. In some embodiments, tracer wire 302 is parallel to pipe 301. In various embodiments, tracer wire 302 is attached to pipe 301 at suitable intervals (e.g., every 6 to 36 inches) using an appropriate technique (e.g., tape, twine, zip-tie, etc.), continuously attached to pipe 301, or attached in any other appropriate manner.

In various embodiments, a pipe (e.g., pipe 101 of FIG. 1, pipe 201 of FIG. 2, and pipe 301 of FIG. 3, etc.) is formed using a non-metallic material including one or more of the following dielectrics: Medium Density Poly-Ethylene (MDPE), High Density Poly-Ethylene (HDPE), Aldyl-A, Poly-Vinyl Chloride (PVC), polyamide, polycarbonate, Poly-Propylene (PP), Poly-Tetra-Fluoro-Ethylene (PTFE), Acrylonitrile Butadiene Styrene (ABS), or any other appropriate material. In various embodiments, an insert pipe (e.g., insert 205 of FIG. 2) is formed using a non-metallic material including one or more of the following dielectrics: MDPE, HDPE, Aldyl-A, PVC, polyamide, polycarbonate, PP, PTFE, ABS, or any other appropriate non-metallic material, or a metallic material including one or more of the following: iron, steel, copper, stainless steel, or any other appropriate metallic material. In various embodiments, a pipe and/or an insert pipe have outer and inner diameters in the range of 0.5 inches to 12 inches where the inner diameter of the pipe is larger than the outer diameter of the insert pipe. In some embodiments, the outer diameter of the insert pipe is in the range of 25% to 90% of the inner diameter of the parent pipe. In various embodiments, a pipe and/or an insert pipe (e.g., pipe 101 of FIG. 1, pipe 201 or FIG. 2, pipe 301 of FIG. 3, and insert 205 of FIG. 2) conform(s) to either Iron Pipe Standard (IPS) or Copper Tubing Standard (CTS) specifications (e.g., is sized according to ¾" IPS SDR11 or ½" CTS×0.90), or any other appropriate standard. In various embodiments, tracer wire 302 is an insulated copper wire in the range of American Wire Gage (AWG) 18 and AWG 8, or any other appropriate diameter.

Transduction Schemes

Figure 4:
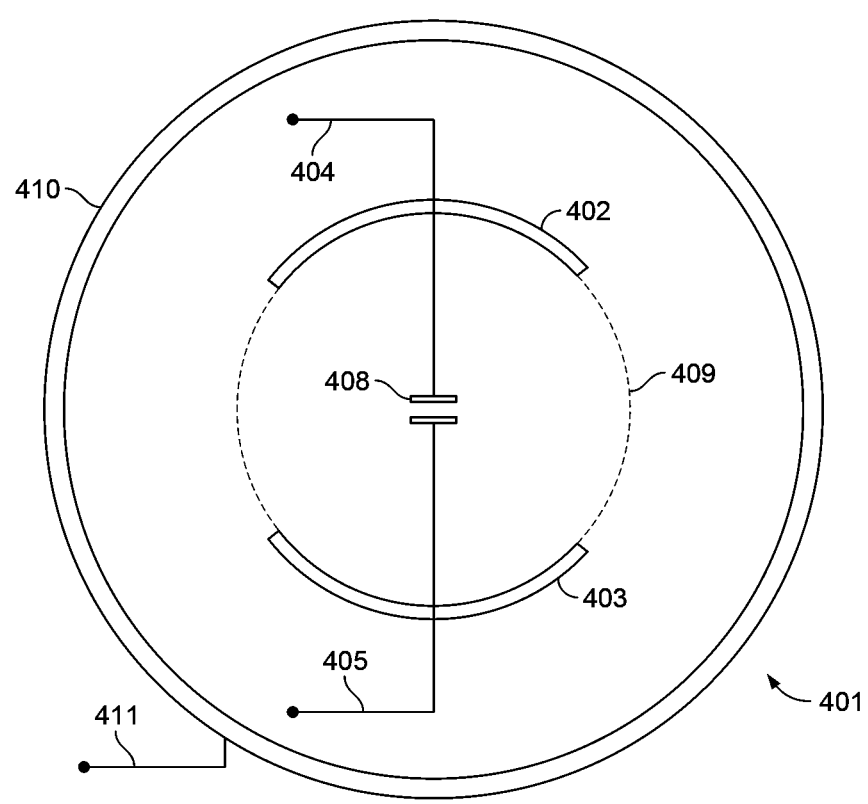
FIG. 4 is a schematic diagram illustrating an embodiment of a cross-sectional view of curved top and bottom capacitive drive and sense electrodes along the periphery of an empty cylindrical volume surrounded by a cylindrical shield electrode.

FIG. 4 is a schematic diagram illustrating an embodiment of a cross-sectional view of curved top and bottom capacitive drive and sense electrodes along the periphery of an empty cylindrical volume surrounded by a cylindrical shield electrode. In various embodiments, cylindrical volume 409 contains vacuum, a liquid such as water, or a gas or combination of gasses including air, natural gas, nitrogen, methane, or any other appropriate liquid and/or gas. In the example shown, two electrode system 401 comprises electrode 402 and electrode 403. Electrode 402 and electrode 403 are electrically-conductive concentric arcs positioned along the periphery of cylindrical volume 409. Shield 410 is an electrically-conductive concentric arc positioned such that in a cross section the arc is positioned around cylindrical volume 409, electrode 402, and electrode 403. Lead 404 is electrically connected to electrode 402. Lead 405 is electrically connected to electrode 403. Applying an electrostatic excitation to lead 404 and lead 405 creates a voltage or current response between electrode 402 and electrode 403, respectively, in proportion to capacitance 408 of cylindrical volume 409, which in turn depends on the dielectric properties of cylindrical volume 409. Thus, information about the dielectric properties of cylindrical volume 409 can be inferred from measurements of the voltage or current response resulting from an electrostatic excitation. In some embodiments, shield 410 isolates electrode 402 and electrode 403 from external EMI. In various embodiments, electrode 402, electrode 403, and shield 410 are formed using an electrically conductive material including one of the following: copper, aluminum, beryllium copper, silver, or any other appropriate material.

Figure 5:
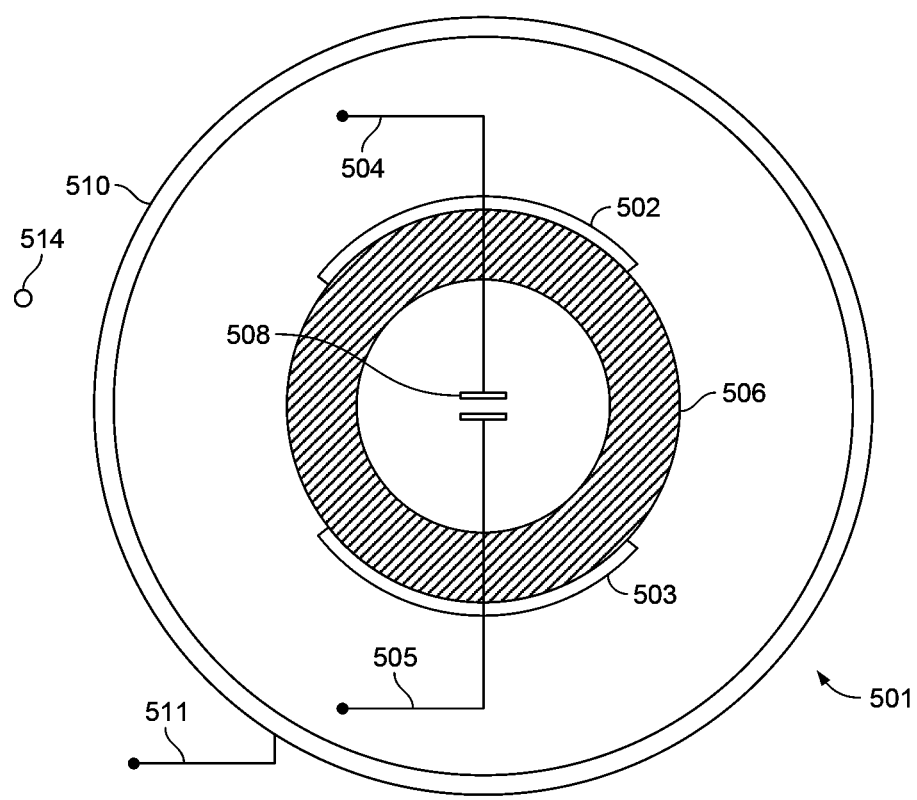
FIG. 5 is a schematic diagram illustrating an embodiment of a cross-sectional view of curved top and bottom capacitive drive and sense electrodes along the periphery of a hollow pipe surrounded by a cylindrical shield electrode.

FIG. 5 is a schematic diagram illustrating an embodiment of a cross-sectional view of curved top and bottom capacitive drive and sense electrodes along the periphery of a hollow pipe surrounded by a cylindrical shield electrode. In some embodiments, a pipe (e.g., pipe 101 of FIG. 1 or pipe 301 of FIG. 3) is measured using two electrode system 501. In the example shown, two electrode system 501 comprises electrode 502 and electrode 503. Electrode 502 and electrode 503 are electrically-conductive concentric arcs positioned along the periphery of pipe 506. Shield 510 is an electrically-conductive concentric arc positioned such that in a cross section the arc is positioned around pipe 506, electrode 502, and electrode 503. Tracer wire 514 is positioned outside of shield 510. Lead 504 is electrically connected to electrode 502. Lead 505 is electrically connected to electrode 503. Applying an electrostatic excitation to lead 504 and lead 505 creates a voltage or current response between electrode 502 and electrode 503, respectively, in proportion to the capacitance 508 of pipe 506, which in turn depends on the dielectric properties of pipe 506 and its contents. Thus, information about the dielectric properties of pipe 506 can be inferred from measurements of the voltage or current response resulting from an electrostatic excitation. In some embodiments, shield 510 isolates electrode 502 and electrode 503 from external EMI including parasitic signals on tracer 514. In various embodiments, electrode 502, electrode 503, and shield 510 are formed using an electrically conductive material including one of the following: copper, aluminum, beryllium copper, silver, or any other appropriate material. In various embodiments, pipe 506 may be formed using a non-metallic material including one or more of the following: MDPE, HDPE, Aldyl-A, PVC, polyamide, polycarbonate, PP, PTFE, ABS, etc. In various embodiments, the cylindrical volume within pipe 506 contains vacuum, a liquid such as water, or a gas or combination of gasses including air, natural gas, nitrogen, methane, or any other appropriate liquid and/or gas. In various embodiments, the annular volume between pipe 506 and shield 510 contains vacuum, a liquid such as water, or a gas or combination of gasses including air, natural gas, nitrogen, methane, or any other appropriate liquid and/or gas.

Figure 6:
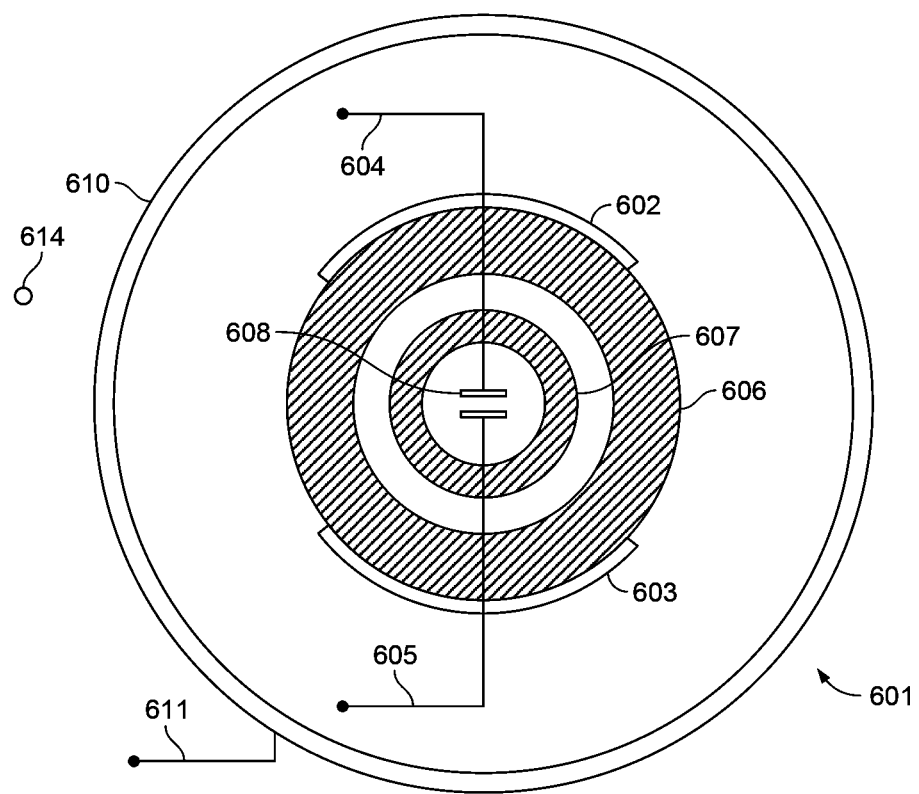
FIG. 6 is a schematic diagram illustrating an embodiment of a cross-sectional view of curved top and bottom capacitive drive and sense electrodes along the periphery of a parent pipe containing a pipe insert and surrounded by a cylindrical shield electrode.

FIG. 6 is a schematic diagram illustrating an embodiment of a cross-sectional view of curved top and bottom drive and sense electrodes along the periphery of a parent pipe containing a pipe insert and surrounded by a cylindrical shield electrode. In some embodiments, a pipe (e.g., pipe 201 of FIG. 2) is measured using two electrode system 601. In the example shown, electrode 602 and electrode 603 are electrically-conductive concentric arcs positioned along the periphery of parent pipe 606. Shield 610 is an electrically-conductive concentric arc positioned such that in a cross section the arc is positioned around pipe 606, electrode 602, and electrode 603. Tracer wire 614 is positioned outside of shield 610. Lead 604 is electrically connected to electrode 602. Lead 605 is electrically connected to electrode 603. Applying an electrostatic excitation to leads 604 and 605 creates a voltage or current response between electrode 602 and electrode 603, respectively, in proportion to the capacitance 608 of parent pipe 606 and pipe insert 607, which in turn depends on the dielectric properties of parent pipe 606 and pipe insert 607. Thus, information about the dielectric properties of parent pipe 606 and pipe insert 607 can be inferred from measurements of the voltage or current response resulting from an electrostatic excitation. In some embodiments, shield 610 isolates electrode 602 and electrode 603 from external EMI including parasitic signals on tracer 614. In various embodiments, electrode 602, electrode 603, and shield 610 are formed using an electrically conductive material including one of the following: copper, aluminum, beryllium copper, silver, or any other appropriate material. In various embodiments, parent pipe 606 is formed using a non-metallic material including one or more of the following: MDPE, HDPE, Aldyl-A, PVC, polyamide, polycarbonate, PP, PTFE, ABS, or any other appropriate non-metallic material, or a metallic material including one or more of the following: iron, steel, copper, stainless steel, or any other appropriate metallic material. In various embodiments, pipe insert 607 is formed using a non-metallic material including one or more of the following: MDPE, HDPE, Aldyl-A, PVC, polyamide, polycarbonate, PP, PTFE, ABS, or any other appropriate non-metallic material. In various embodiments, the cylindrical volume within pipe insert 607 contains vacuum, a liquid such as water, or a gas or combination of gasses including air, natural gas, nitrogen, methane, or any other appropriate liquid, gas, or combination of liquids and/or gases. In various embodiments, the interstitial volume between parent pipe 606 and pipe insert 607 and the cylindrical volume within pipe insert 607 each contain vacuum, a liquid such as water, or a gas or combination of gasses including air, natural gas, nitrogen, methane, or any other appropriate gas. In various embodiments, the annular volume between pipe 606 and shield 610 contains vacuum, a liquid such as water, or a gas or combination of gasses including air, natural gas, nitrogen, methane, or any other appropriate gas.

Figure 7A:
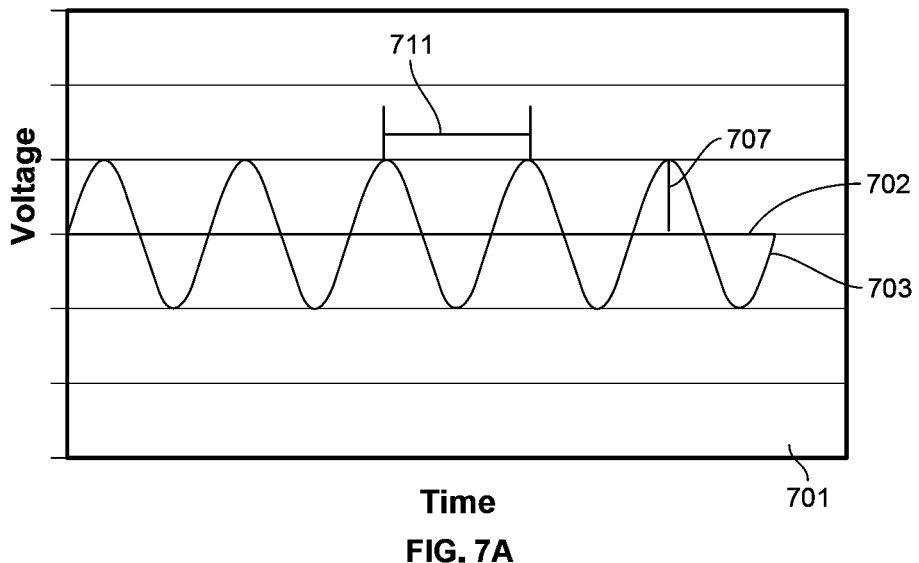
FIG. 7A is a graph illustrating an embodiment of a periodic drive voltage waveform referenced to a ground potential.

FIG. 7A is a graph illustrating an embodiment of periodic drive voltage waveform referenced to a ground potential. In some embodiments, the waveform of FIG. 7A is used to drive a two electrode system (e.g., two electrode system 401 of FIG. 4, two electrode system 501 of FIG. 5, or two electrode system 601 of FIG. 6). In the example shown, drive voltage waveform 703 is applied having period 711 and amplitude 707 relative to ground potential 702. In some embodiments, drive voltage waveform 703 has amplitude in the range of 1 mV to 100 V, and frequency in the range of 1 kHz to 10 MHz.

Figure 7B:
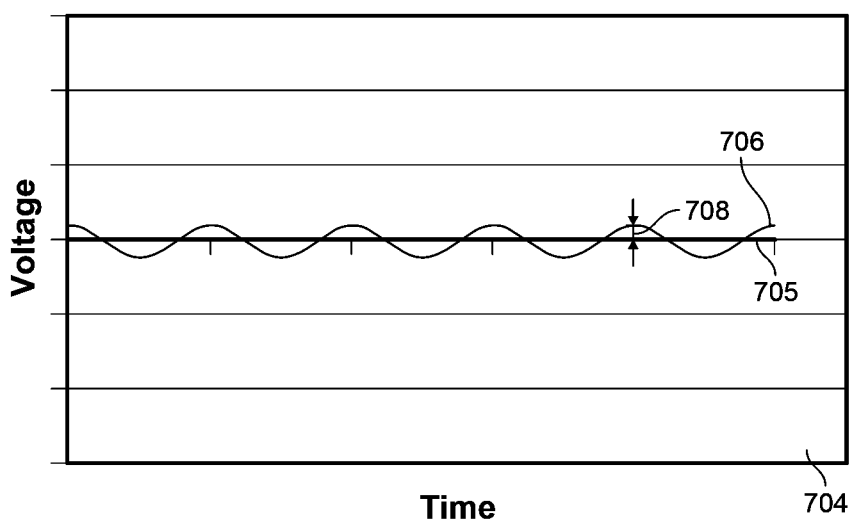
FIG. 7B is a graph illustrating an embodiment of a periodic sense voltage waveform referenced to a ground potential.

FIG. 7B is a graph illustrating an embodiment of periodic sense voltage waveform referenced to a ground potential. In some embodiments, the waveform of FIG. 7B is measured in response to a drive waveform (e.g., a drive waveform of FIG. 7A) of a two electrode system (e.g., two electrode system 401 of FIG. 4, two electrode system 501 of FIG. 5, or two electrode system 601 of FIG. 6). In the example shown, a drive voltage waveform (e.g., drive voltage waveform 703 of FIG. 7A) results in sense electrical waveform 706 having the same period 711 as the drive waveform, but with amplitude 708 relative to ground potential 705. In some embodiments, a drive voltage waveform and a sense electrical waveform are shifted in phase relative to one another. In various embodiments, sense voltage waveform 706 has amplitude in the range of 1 mV to 100 V, and frequency in the range of 1 kHz to 10 MHz.

Figure 8A:
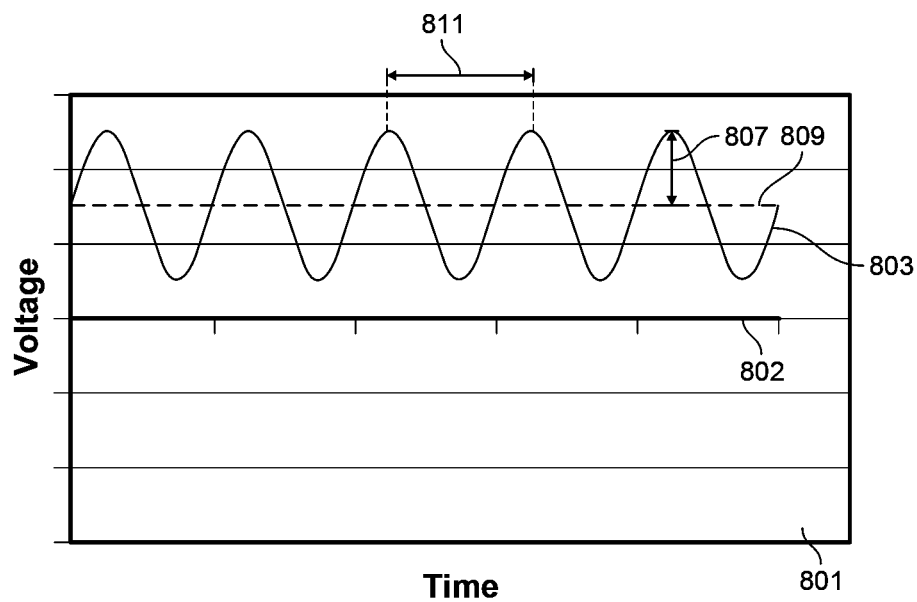
FIG. 8A is a graph illustrating an embodiment of a periodic drive voltage waveform referenced to a bias potential.

FIG. 8A is a graph illustrating an embodiment of periodic drive voltage waveform referenced to a bias potential. In some embodiments, the waveform of FIG. 8A is used to drive a two electrode system (e.g., two electrode system 401 of FIG. 4, two electrode system 501 of FIG. 5, or two electrode system 601 of FIG. 6). In the example shown, drive voltage waveform 803 is applied having period 811 and amplitude 807 relative to bias potential 809. In some embodiments, drive voltage waveform 803 has amplitude in the range of 1 mV to 100 V, bias potential 809, and frequency in the range of 1 kHz to 10 MHz.

Figure 8B:
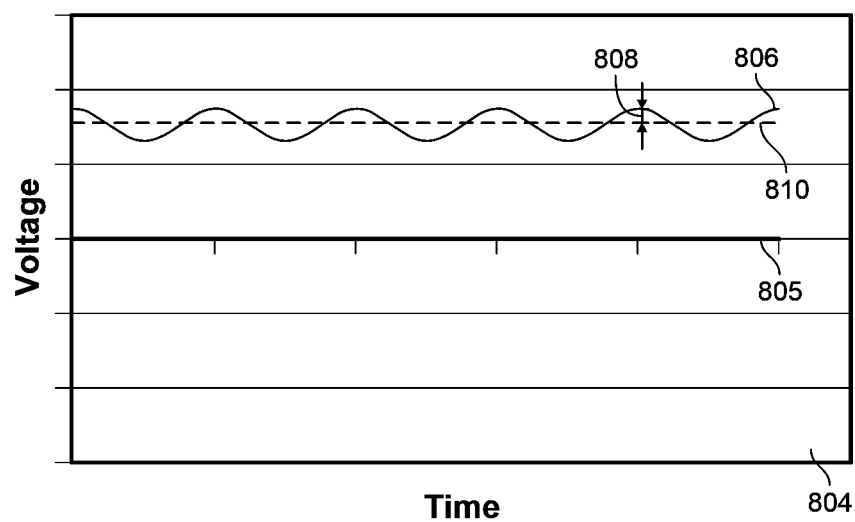
FIG. 8B is a graph illustrating an embodiment of a periodic sense voltage waveform referenced to a bias potential.

FIG. 8B is a graph illustrating an embodiment of periodic sense voltage waveform referenced to a bias potential. In some embodiments, the waveform of FIG. 8B is measured in response to a drive waveform (e.g., a drive waveform of FIG. 8A) of a two electrode system (e.g., two electrode system 401 of FIG. 4, two electrode system 501 of FIG. 5, or two electrode system 601 of FIG. 6). In the example shown, drive voltage waveform (e.g., drive voltage waveform 803 of FIG. 8A) results in sense electrical waveform 806 having the same period 811 as drive waveform 803, but with amplitude 808 relative to bias potential 810. In some embodiments, a drive voltage waveform and sense electrical waveform are shifted in phase relative to one another. In various embodiments, sense voltage waveform 806 has amplitude in the range of 1 mV to 100 V, bias potential in the range of 1 mV to 100 V, and frequency in the range of 1 kHz to 10 MHz.

In some embodiments, an electrical response waveform to a drive voltage waveform is a current waveform having an amplitude, the same frequency as a drive voltage waveform, and a phase shift relative to a drive voltage waveform. The magnitude and phase of the response current for a given drive voltage depends on the complex impedance of the load in accordance with Ohm's law.

Figure 9A:
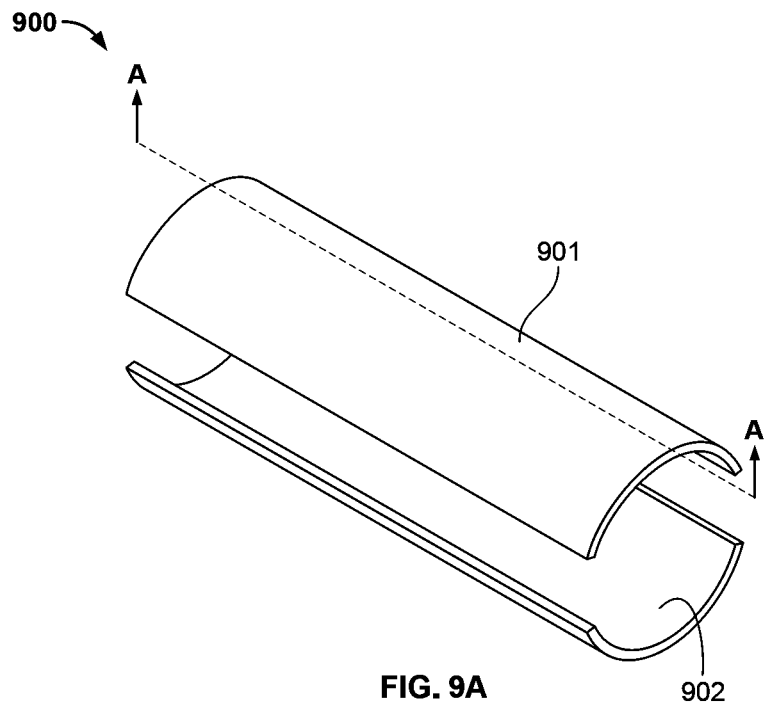
FIGS. 9A & 9B are a schematic diagram illustrating an isometric view and a corresponding cross-sectional view of an embodiment of a two electrode system for supporting thickness field excitation within a cylindrical volume.
Figure 9B:
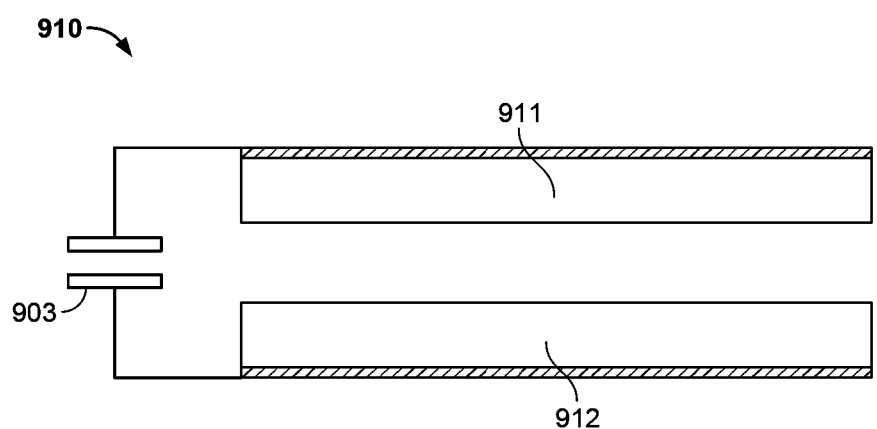

FIGS. 9A & 9B are a schematic diagram illustrating an isometric view (FIG. 9A) and a corresponding cross-sectional view (FIG. 9B) of an embodiment of a two electrode system for supporting thickness field excitation within a cylindrical volume. In some embodiments, two electrode system 900 of FIG. 9A and two electrode system 910 of FIG. 9B are used to implement two electrode systems of FIG. 4, FIG. 5, or FIG. 6. In the example shown, electrode 901 and electrode 902 of FIG. 9A and electrode 911 and electrode 912 of FIG. 9B are electrically-conductive concentric sections of a cylindrical shell positioned along the periphery of a corresponding cylindrical volume. The resulting capacitance (e.g., capacitance 903 of FIG. 9B) between electrode 901 and electrode 902 or electrode 911 and electrode 912 depends on the dielectric properties of the contents of the enclosed cylindrical volume. Accordingly, the dielectric properties of the contents of the enclosed cylindrical volume are inferred from measurements of capacitance 903. In various embodiments of a pipe insert sensor, the contents of the enclosed cylindrical volume include a sample pipe or a pipe insert within a sample parent pipe, or any other appropriate combination of pipes. Thus, the presence or absence of a pipe insert within a sample pipe is inferred from measurements of capacitance 903. For example, capacitance 903 is compared to previously determined values corresponding to the capacitance of a sample pipe with no insert or a sample pipe containing an insert. In some embodiments, a library of values are stored of measurements with sample pipes of different thicknesses with different insert thicknesses at different temperatures and these are matched to measured values. In some embodiments, the stored measurements comprise a family of measurements at different frequencies and the sensed response spectra are matched to stored measurements to establish whether there is an insert or no insert in a sample pipe. In some embodiments, a threshold is determined between a group of measurements of a sample with and without an insert and the threshold is used to determine whether a sample has an insert or not. In some embodiments, a boundary between two clusters of spectra of a sample with and without an insert is determined and used to determine whether a sample has an insert or not.

Figure 10A:
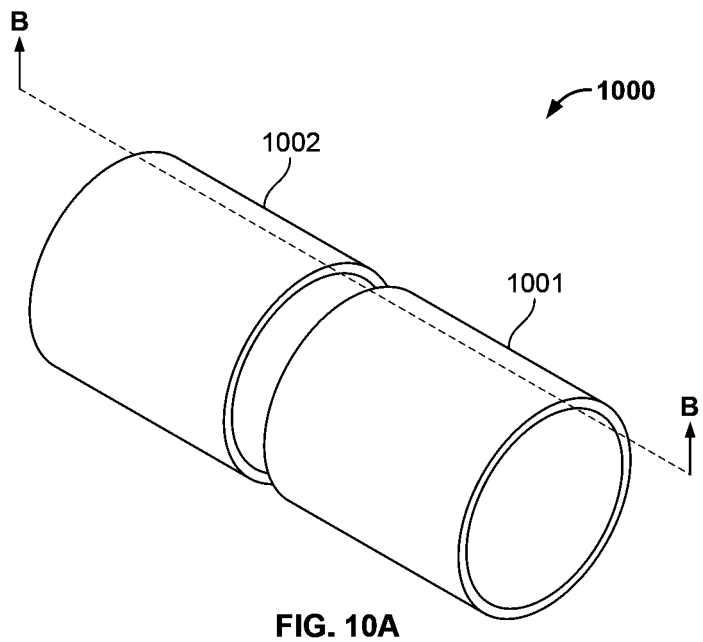
FIGS. 10A & 10B are a schematic diagram illustrating an isometric view and a corresponding cross-sectional view of an embodiment of a two electrode system for supporting lateral field excitation within a cylindrical volume.
Figure 10B:
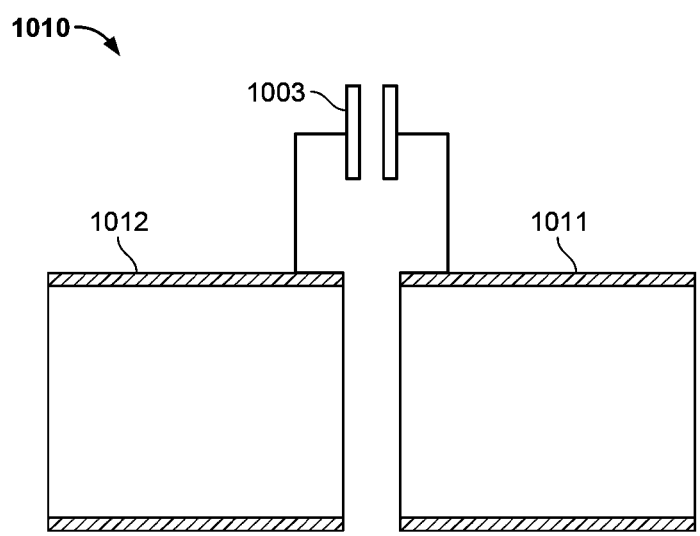

FIGS. 10A & 10B are a schematic diagram illustrating an isometric view (FIG. 10A) and a corresponding cross-sectional view (FIG. 10B) of an embodiment of a two electrode system for supporting lateral field excitation within a cylindrical volume. In the example shown, electrode 1001 and electrode 1002 of FIG. 10A and electrode 1011 and electrode 1012 of FIG. 10B are electrically-conductive concentric sections of a cylindrical shell positioned along the periphery of a corresponding cylindrical volume. The resulting capacitance (e.g., capacitance 1003 of FIG. 10B) between electrode 1001 and electrode 1002 or electrode 1011 and 1012 depends on the dielectric properties of the contents of the enclosed cylindrical volume. Accordingly, the dielectric properties of the contents of the enclosed cylindrical volume are inferred from measurements of capacitance 1003. In various embodiments of a pipe insert sensor, the contents of the enclosed cylindrical volume include a sample pipe or a pipe insert within a sample parent pipe, or any other appropriate combination of pipes. Thus, the presence or absence of a pipe insert within a sample is be inferred from measurements of capacitance 1003. For example, capacitance 1003 is compared to previously determined values corresponding to the capacitance of a sample pipe with no insert or a sample pipe containing an insert. In some embodiments, a library of values are stored of measurements with sample pipes of different thicknesses with different insert thicknesses at different temperatures and these are matched to measured values. In some embodiments, the stored measurements comprise a family of measurements at different frequencies and the sensed response spectra are matched to stored measurements to establish whether there is an insert or no insert in a sample pipe. In some embodiments, a threshold is determined between a group of measurements of a sample with and without an insert and the threshold is used to determine whether a sample has an insert or not. In some embodiments, a boundary between two clusters of spectra of a sample with and without an insert is determined and used to determine whether a sample has an insert or not.

Figure 11A:
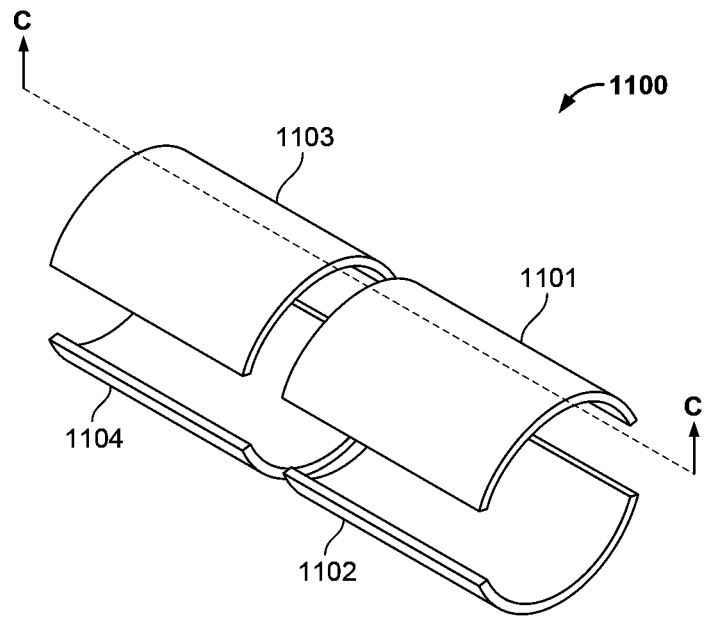
FIGS. 11A & 11B are a schematic diagram illustrating an isometric view and a corresponding cross-sectional view of an embodiment of a four electrode system for supporting thickness field and lateral field excitation within a cylindrical volume.
Figure 11B:
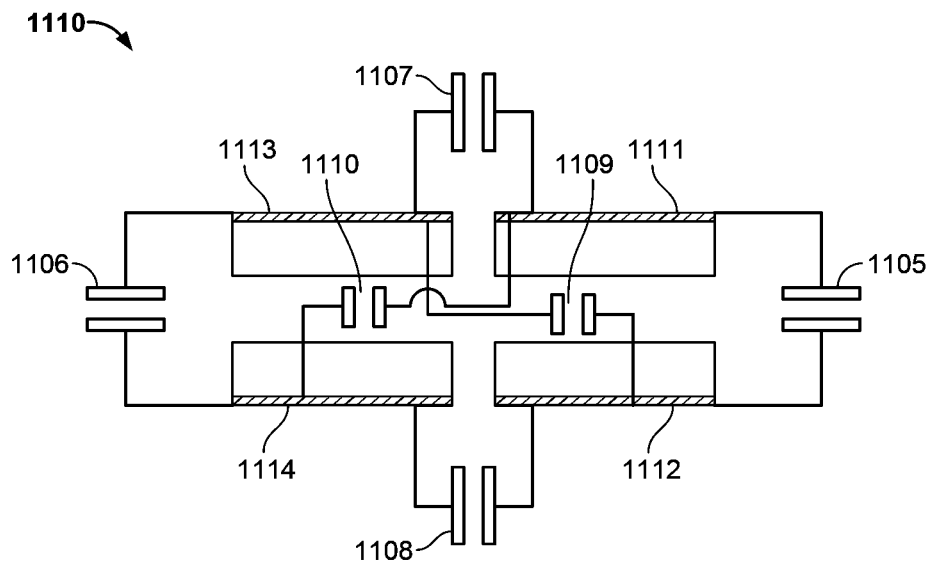

FIGS. 11A & 11B are a schematic diagram illustrating an isometric view (FIG. 11A) and a corresponding cross-sectional view (FIG. 11B) of an embodiment of a four electrode system for supporting thickness field and lateral field excitation within a cylindrical volume. In the example shown, electrode 1101, electrode 1102, electrode 1103 and electrode 1104 of FIG. 11A and electrode 1111, electrode 1112, electrode 1113 and electrode 1114 of FIG. 11B are electrically-conductive concentric sections of a cylindrical shell positioned along the periphery of a corresponding cylindrical volume. The depicted arrangement results in: capacitance 1105 between electrode 1101 and electrode 1102 or 1111 and electrode 1112, capacitance 1106 between electrode 1103 and electrode 1104 electrode 1113 and electrode 1114, capacitance 1107 between electrode 1101 and electrode 1103 or electrode 1111 and electrode 1113, capacitance 1108 between electrode 1102 and electrode 1104 or electrode 1112 and electrode 1114, capacitance 1109 between electrode 1102 and electrode 1103 or electrode 1112 and electrode 1113, and capacitance 1110 between electrode 1101 and electrode 1104 or electrode 1111 and electrode 1114. Each of the resulting capacitances (e.g., capacitance 1105, capacitance 1106, capacitance 1107, capacitance 1108, capacitance 1109, and capacitance 1110) depends on the dielectric properties of the contents of the enclosed cylindrical volume. Accordingly, the dielectric properties of the contents of the enclosed cylindrical volume are inferred from measurements of the capacitances. In various embodiments of a pipe insert sensor, the contents of the enclosed cylindrical volume include a sample pipe or a pipe insert within a sample parent pipe, or any other appropriate combination of pipes. Thus, the presence or absence of a pipe insert within a sample pipe is inferred from measurements of capacitance 1105, capacitance 1106, capacitance 1107, capacitance 1108, capacitance 1109, and capacitance 1110. For example, each of capacitance 1105, capacitance 1106, capacitance 1107, capacitance 1108, capacitance 1109, and capacitance 1110 is compared to previously determined values corresponding to the capacitance of a sample pipe with no insert or a sample pipe containing an insert. In some embodiments, a library of values are stored of measurements with sample pipes of different thicknesses with different insert thicknesses at different temperatures and these are matched to measured values. In some embodiments, the stored measurements comprise a family of measurements at different frequencies and the sensed response spectra are matched to stored measurements to establish whether there is an insert or no insert in a sample pipe. In some embodiments, a threshold is determined between a group of measurements of a sample with and without an insert and the threshold is used to determine whether a sample has an insert or not. In some embodiments, a boundary between two clusters of spectra of a sample with and without an insert is determined and used to determine whether a sample has an insert or not.

Figure 12:
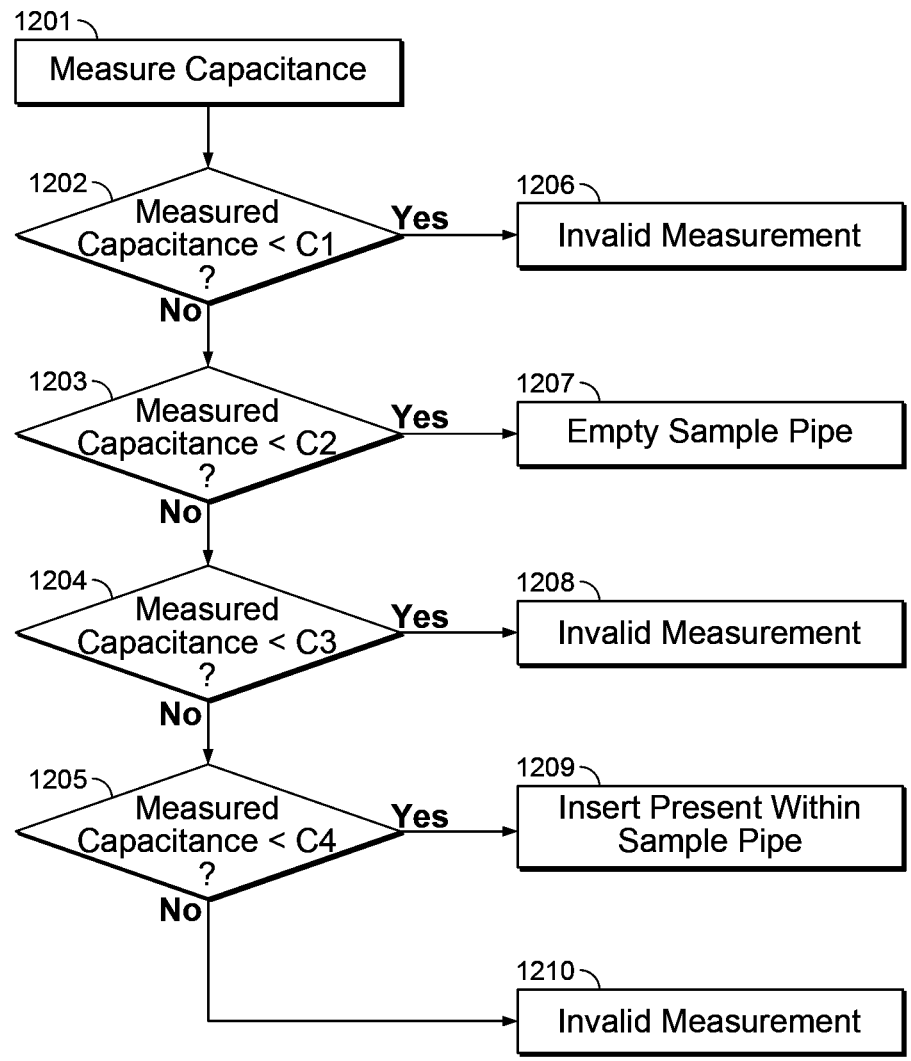
FIG. 12 is a flow diagram illustrating an embodiment of a procedure for determining the presence or absence of an insert within a parent pipe based on comparing a measured capacitance value to a series of previously determined ones.

FIG. 12 is a flow diagram illustrating an embodiment of a procedure for determining the presence or absence of a dielectric insert within a parent pipe based on comparing a measured capacitance value to a series of previously determined ones. In some embodiments, the process of FIG. 12 is used to determine the presence or absence of an insert in a two electrode system of FIG. 4, FIG. 5, or FIG. 6. In some embodiments, prior to initiating a measurement, threshold capacitance values are stored (e.g., in a non-volatile memory) for use by a processor. For example, threshold capacitance C1 corresponds to the lower limit of the measured capacitance of an empty pipe sample (i.e., one not containing an insert), threshold capacitance C2 corresponds to the upper limit of the measured capacitance of an empty pipe sample, threshold capacitance C3 corresponds to the lower limit of the measured capacitance of a pipe sample containing a pipe insert, and threshold capacitance C4 corresponds to the upper limit of the measured capacitance of a pipe sample containing a pipe insert. In various embodiments of the device, the values of C1, C2, C3, and C4 are determined a-priori using a separate capacitance measurement instrument, the insert sensor itself, or any other appropriate measurement device or calculation technique. In the example shown, in 1201 a capacitance measurement of a sample pipe is performed to determine a measured capacitance value. For example, a drive sinusoidal voltage is applied at a given amplitude and frequency, and a current or voltage amplitude and phase response is measured and used to determine a capacitance value. Subsequently, in 1202, it is determined whether the measured capacitance value is less than C1. In the event that the measured value is less than C1, in 1206 it is indicated that the measurement is invalid and the process ends. For example, a user is informed that a measurement is invalid (e.g., a light is lit, a sound is emitted, a text error message is displayed on a screen, etc.). In the event that the measured value is not less than C1, then control passes to 1203. In 1203, it is determined whether the measured capacitance is less than C2. In the event that the measured capacitance is less than C2, in 1207 it is indicated that the sample pipe is empty, and the process ends. For example, a measured value of capacitance between C1 and C2 causes the system to indicate that there is no insert pipe in the sample pipe (e.g., an indicator light is lit, a sound is generated, a text is displayed on a display, etc.). In the event that the measured capacitance is not less than C2, then control passes to 1204. In 1204, it is determined whether the measured capacitance is less than C3. In the event that the measured capacitance is less than C3, in 1208 it is indicated that the measurement is invalid, and the process ends. For example, a user is informed that a measurement is invalid (e.g., a light is lit, a sound is emitted, a text error message is displayed on a screen, etc.). In the event that a measured capacitance value is not less than C3, control passes to 1205. In 1205, it is determined whether the measured capacitance value is less than C4. In the event that the measured capacitance value is less than C4, in 1209 it is indicated that there is a pipe insert inside the sample pipe, and the process ends. For example, a measured capacitance value between C3 and C4 indicates that an insert pipe is within the sample pipe. In various embodiments, a user is informed that there is an insert pipe with the sample pipe by one or more of the following: lighting a light indication, sounding a sound indication, displaying a text or other icon indication on a display, or any other appropriate indication. In the event that the measured capacitance is not less than C4, it is indicated that the measurement is invalid, and the process ends.

In some embodiments, the values of capacitances C1, C2, C3, and C4 are functions of a measured temperature (e.g., as determined by a temperature sensor onboard the device). In some embodiments, a different set of C1, C2, C3, and C4 values are used to detect electrically conductive inserts within a parent.

Figure 13:
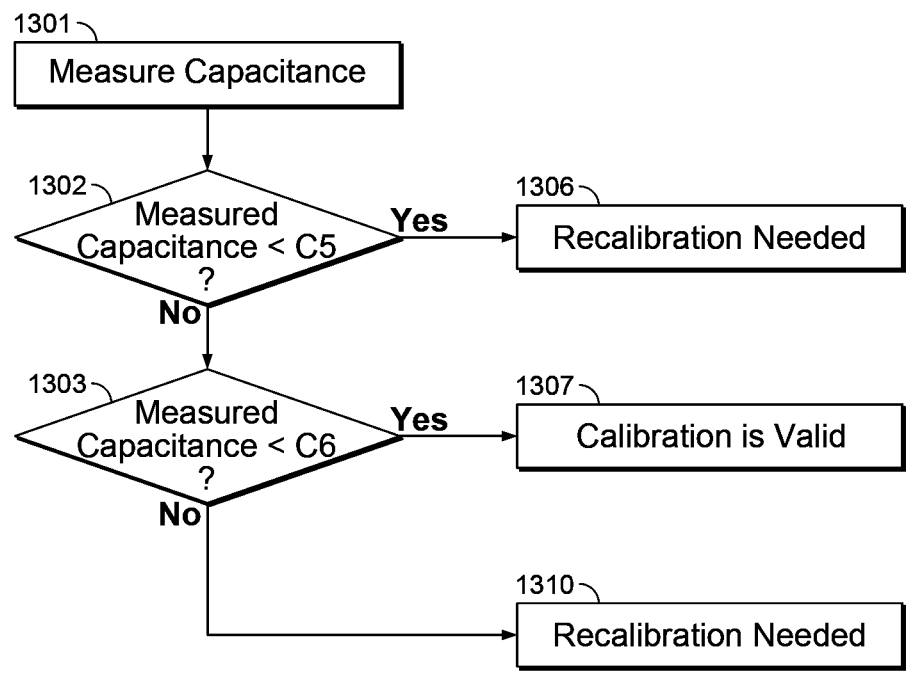
FIG. 13 is a flow diagram illustrating an embodiment of a self-test procedure for validating the calibration of a capacitive pipe insert detection instrument based on comparing a measured capacitance value to a series of previously determined ones.

FIG. 13 is a flow diagram illustrating an embodiment of a self-test procedure for validating the calibration of a capacitive pipe insert detection instrument based on comparing a measured capacitance value to a series of previously determined ones. In some embodiments, the process of FIG. 13 is used to validate a calibration of a two electrode system of FIG. 4, FIG. 5, or FIG. 6. In some embodiments, prior to initiating a self-test procedure, threshold capacitance values are stored (e.g., in a non-volatile memory) for use by a processor. For example, threshold capacitances C5 and C6 correspond to the lower and upper limit, respectively, of the measured capacitance of an empty instrument (i.e., one not containing pipe and/or an insert) in the closed configuration. In various embodiments, the values of C5 and C6 are determined a-priori using a separate capacitance measurement instrument, the insert sensor itself, or any other appropriate device or calculation technique. In the example shown, in 1301 a capacitance measurement of the empty instrument is performed to determine a measured capacitance value. For example, a drive sinusoidal voltage is applied at a given amplitude and frequency, and a current or voltage amplitude and phase response is measured and used to determine a capacitance value of the instrument without a sample inside. Subsequently, in 1302, it is determined whether the measured capacitance value is less than C5. In the event that the measured capacitance value is less than C5, then in 1306 it is indicated that recalibration is needed, and the process ends. For example, a message is displayed on a display that the self-test has failed and recalibration is required. In the event that the measured capacitance value is not less than C5, then in 1303 it is determined whether the measured capacitance value is less than C6. In the event that the measure capacitance value is less than C6, then in 1307 it is indicated that calibration is valid and the process ends. For example, a message is displayed on a display that the self-test has succeeded and the calibration is valid. In the event that the measured capacitance value is not less than C6, then in 1310 it is indicated that the recalibration is needed and the process ends. For example, a message is displayed on a display that the self-test has failed and recalibration is required. In some embodiments, the values of capacitances C5 and C6 are functions of a measured temperature (e.g., as determined by a temperature sensor onboard the device).

System Implementation

Figure 14:
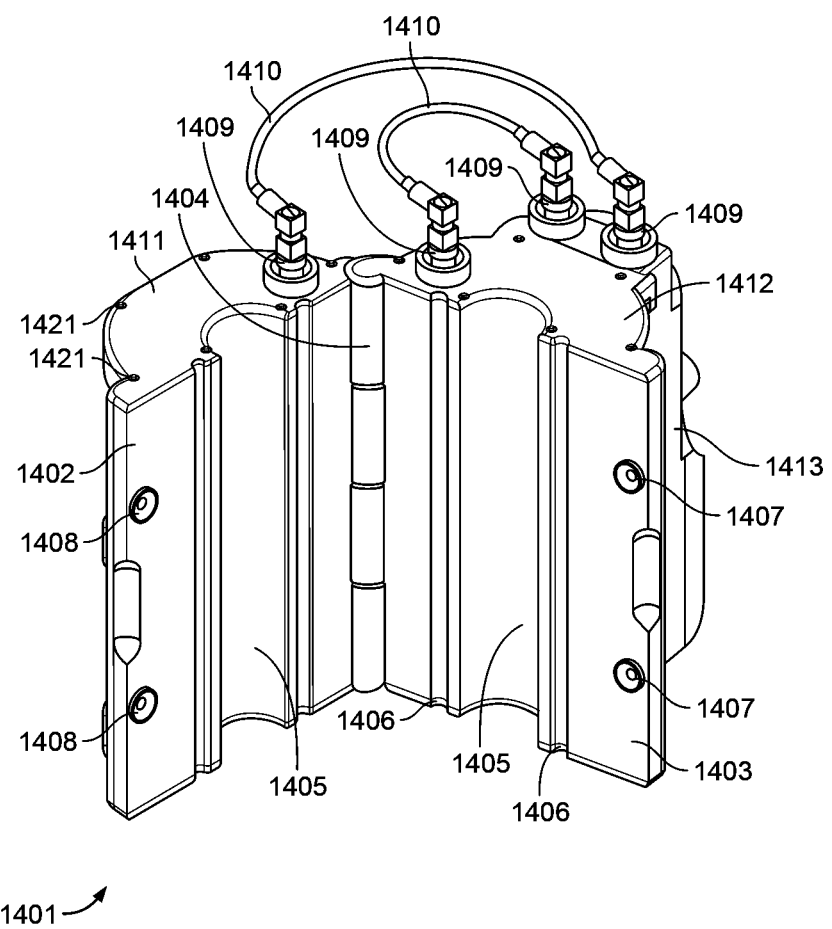
FIG. 14 is a schematic diagram illustrating an isometric view of an embodiment of a capacitive pipe insert detection instrument in an open configuration.

FIG. 14 is a schematic diagram illustrating an isometric view of an embodiment of a capacitive pipe insert detection instrument in an open configuration. In some embodiments, the device of FIG. 14 is used to implement a calibration of a two electrode system of FIG. 4, FIG. 5, or FIG. 6. In the example shown, instrument 1401 is in an unclamped or open configuration. Instrument 1401 comprises enclosure part 1402, enclosure part 1403, and console 1413. Enclosure part 1402, enclosure part 1403, and console 1413 house components and sub-systems that are used to perform sensing, processing, and communication functions. Console 1413 is attached to enclosure part 1403. Hinge 1404 constrains relative motion between enclosure part 1402 and enclosure part 1403 to a single revolute degree of freedom. Enclosure part 1402 and enclosure part 1403 can be closed "clamshell-style" about hinge 1414 such that instrument 1401 is positioned to make measurements on a sample pipe. In various embodiments, hinge 1414 is monolithically co-fabricated as part of enclosure part 1402 and/or enclosure part 1403, formed using one of or a combination of the following materials: steel, stainless steel, aluminum, plastic, brass, bronze, or any other appropriate material, or formed or fabricated in any other appropriate manner.

In the example shown in FIG. 14, enclosure part 1402 and enclosure part 1403 are retained in a clamped or closed configuration using latch feature 1407 and latch feature 1408. Latch feature 1407 and latch feature 1408 comprise pairs of annular magnets attached to a flange on enclosure part 1402 and enclosure part 1403, respectively, using countersunk screws. The polarity of the opposing pairs of magnets is such that a resulting magnetic force of attraction exerts a clamping force that acts to keep enclosure part 1402 and enclosure part 1403 in a clamped or closed position. In various embodiments, latch feature 1407 and latch feature

1408 comprise one or more of the following: a snap, a clasp, an adhesive, hook-and-loop fastener, a screw, or any other appropriate latch feature.

In the example shown, enclosure part 1402 and enclosure part 1403 have curved inner surfaces 1405 that are sized to position instrument 1401 around the periphery of a pipe sample of the corresponding outer diameter In some embodiments, curved inner surfaces 1405 that are sized to accommodate a pipe that conforms to Iron Pipe Standard (IPS), Copper Tubing Standard (CTS) specifications, or any other appropriate standard (e.g., IPS ¾", IPS 1½", CTS ½", etc.). In some embodiments, inner surfaces 1405 have a surface finish to impart a desired coefficient of friction between enclosure part 1402 and enclosure part 1403 and a pipe sample. In various embodiments, inner surfaces 1405 are striated, knurled, pebbled, at least partially covered with rubber-like material, or have any other appropriate surface finish.

In the example shown in FIG. 14, enclosure part 1402 and enclosure part 1403 have curved cutout surfaces 1406 that are sized to position instrument 1401 around the periphery of a tracer wire of having compatible outer diameter (e.g., in the range of AWG 24 and AWG 4.). In some embodiments, inner surfaces 1406 have a surface finish to impart a desired coefficient of friction between enclosure part 1402 and enclosure part 1403 and a tracer wire. In various embodiments, inner surfaces 1406 are striated, knurled, pebbled, at least partially covered with rubber-like material, or have any other surface finish to impart the desired friction.

In the example shown in FIG. 14, end cap 1411 and end cap 1412 form part of the enclosure at the axial ends of enclosure part 1402 and enclosure part 1403, respectively. End cap 1411 is connected to enclosure part 1402 using screws 1421. In various embodiments, end cap 1411 and end cap 1412 are connected to enclosure part 1402 and enclosure part 1403, respectively, using an adhesive, welding or brazing process, monolithically co-fabricated, or using any other appropriate fabrication manner. In some embodiments, End cap 1411 and end cap 1412, and console 1413 are shielded against EMI. End cap 1411 and end cap 1412, and console 1413 include feedthrough connectors 1409 to support passing electrical signals (e.g., a control signal, an electrostatic excitation, and/or response voltages or currents) from within enclosure part 1402 and enclosure part 1403 to console 1413. In various embodiments, connectors 1409 are standard coaxial RF connectors (e.g., a Bayonet Neill-Concelman (BNC), SubMiniature version A (SMA), SubMiniature version B (SMB), SubMiniature version C (SMC), micro coaxial (MCX), micro-miniature coaxial (MMCX) connector, etc.) with a central signal-carrying conductor surrounded by a groundable coaxial shield to reduce EMI. In various embodiments, connectors 1409 on end cap 1411 and end cap 1412 are connected to connectors 1409 on console 1413 by corresponding coaxial cables 1410. In various embodiments, cables 1410 are standard coaxial RF cables (e.g., a RG58, RG59, RG62, RG179, RG180, RG316, etc.) with a central signal-carrying conductor surrounded by a groundable coaxial shield to reduce EMI. In some embodiments, connectors 1409 correspond to electrical drive and sense ports for capacitive measurements. In some embodiments, the outer shield of coaxial cable 1410 is connected to a shield electrode within instrument 1401.

In various embodiments, enclosure part 1402, enclosure part 1403, end cap 1411, end cap 1412, and console 1413 are formed using one or a combination of the following materials: Poly-Lactic Acid (PLA), High-Impact Poly-Styrene (HIPS), HDPE, PVC, polyamide, polycarbonate, PTFE, ABS, urethane, aluminum, steel stainless steel, or any other appropriate material(s). In various embodiments, enclosure part 1402, enclosure part 1403, end cap 1411, end cap 1412, and console 1413 are formed using one or a combination of the following fabrication processes: injection molding, casting, 3-Dimensional printing (e.g., fused deposition manufacturing, selective laser sintering, stereolithography, etc.), blow molding, extrusion, subtractive machining, bending, or any other appropriate fabrication process.

Figure 15:
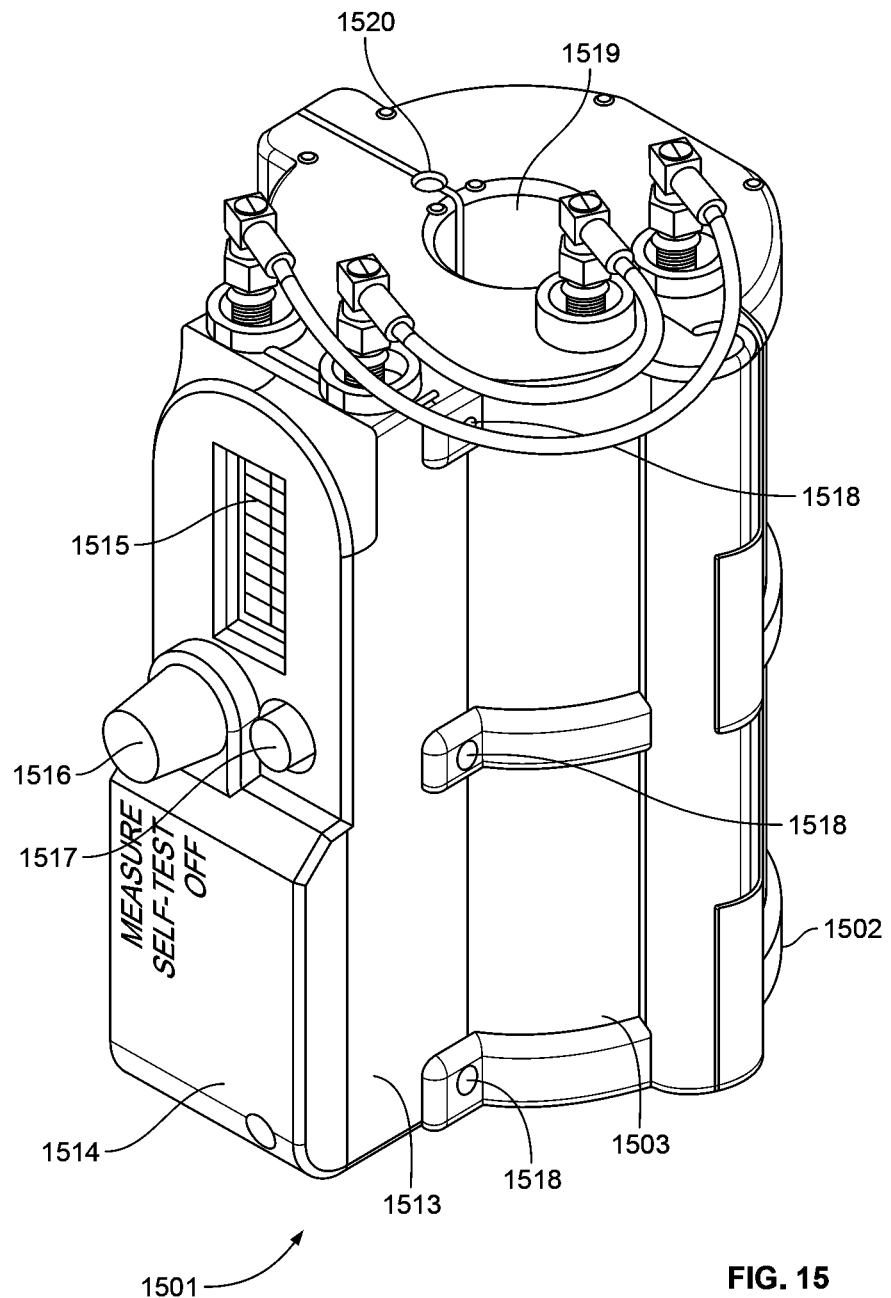
FIG. 15 is a schematic diagram illustrating an isometric view of an embodiment of a capacitive pipe insert detection instrument in a closed configuration.

FIG. 15 is a schematic diagram illustrating an isometric view of an embodiment of a capacitive pipe insert detection instrument in a closed configuration. In some embodiments, the instrument of FIG. 15 is a closed version of the instrument shown in FIG. 14. In the example shown, instrument 1501 is shown clamped or closed. Console 1513 houses electronics for sensing, signal processing, power management, etc., and a user interface. In some embodiments, the electronics are positioned on a Printed Circuit Board (PCB). Console 1513 houses a user interface comprising LCD display 1515, button 1517, and knob 1516, and is connected to enclosure part 1503 using screws 1518. In various embodiments, console 1513 comprises an indicator light, a speaker for emitting a sound indication, a display for a display indication, or any other appropriate device(s) for providing a user an indication. In various embodiments, console 1513 comprises a touchscreen for receiving touch input, a proximity sensor for receiving a gesture input, an inertial sensor for receiving a motion or orientation input, or any other appropriate device(s) for receiving input from a user. In various embodiments, console 1513 is connected to enclosure part 1503 using an adhesive, welding or brazing process, or monolithically co-fabricated, or in any other appropriate manner. Button 1517 is used to initiate a measurement when prompted by LCD display 1515, and knob 1516 is used to select between various modes (e.g., off, self-test, measure, debug, etc.) supported by a processor. Battery compartment lid 1514 is attached to console 1513. In various embodiments, a user interface for the device includes one or more of the following: a button, a toggle switch, a knob, a rotary switch, a rocker switch, a photodetector, a Liquid Crystal Display (LCD), a Light Emitting Diode (LED) display, an Organic LED (OLED) display, an electrophoretic ink display, a capacitive switch, an accelerometer, an ultrasonic transducer, a microphone, a loudspeaker, or any other appropriate user interface component. In various embodiments, enclosure part 1502 and enclosure part 1503 include cutouts that, when the instrument is in a clamped or closed configuration, form channel 1519 and channel 1520 that accommodate a parent pipe and a tracer wire, respectively.

Figure 16:
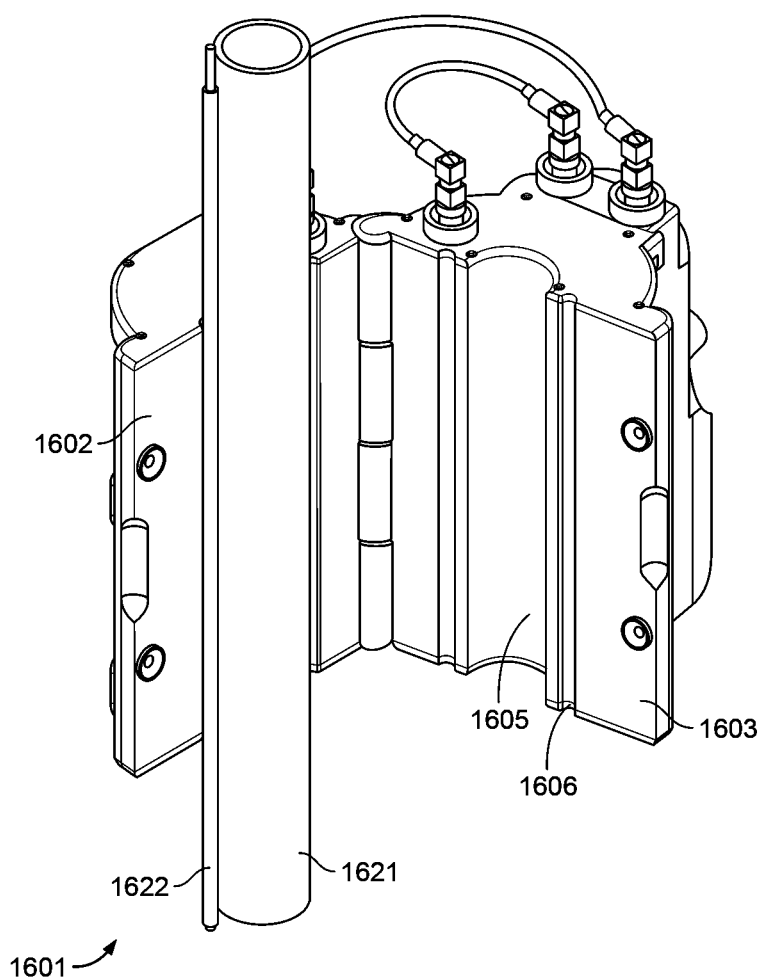
FIG. 16 is a schematic diagram illustrating an isometric view of an embodiment of a capacitive pipe insert detection instrument positioned in an open configuration on a length of pipe and a length of tracer wire.

FIG. 16 is a schematic diagram illustrating an isometric view of an embodiment of a capacitive pipe insert detection instrument positioned in an open configuration on a length of pipe and a length of tracer wire. In some embodiments, the instrument of FIG. 16 comprises the instrument of FIG. 14 shown with a sample pipe and tracer wire. In the example shown, instrument 1601 is shown in an unclamped or open configuration around empty sample pipe 1621 fitted with tracer wire 1622. Sample pipe 1621 and tracer wire 1622 are positioned within cutout 1605 and cutout 1606, respectively, in the event that the instrument is closed, and thus isolated from one another as the enclosure is clamped in the closed position. By interacting with a user interface, an operator activates the instrument to determine the presence or absence of a pipe insert without compromising the integrity of sample pipe 1621 (e.g., an outer parent pipe).

Figure 17:
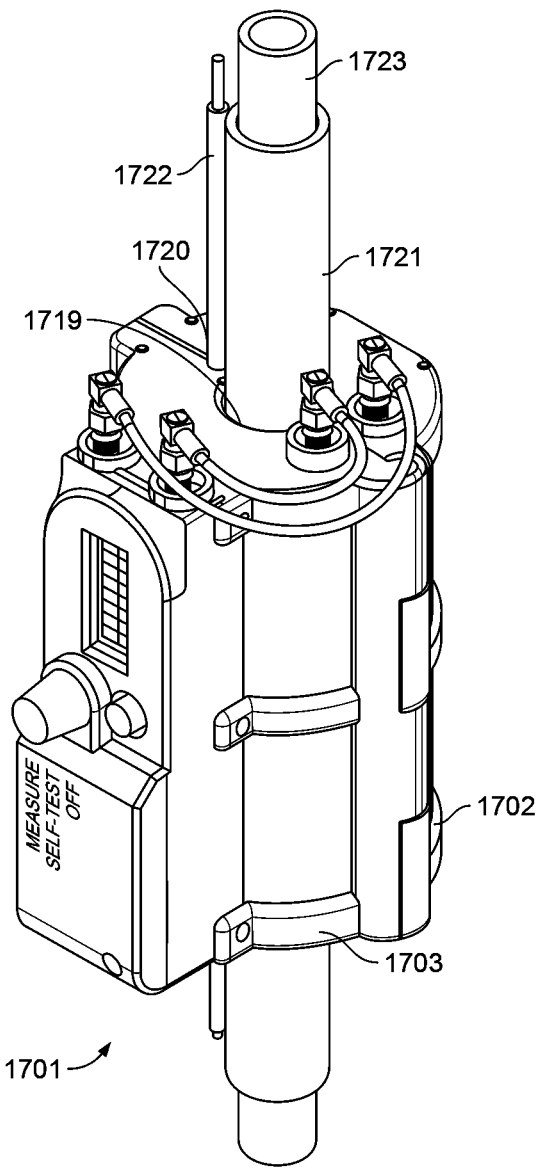
FIG. 17 is a schematic diagram illustrating an isometric view of an embodiment of a capacitive pipe insert detection instrument positioned in a closed configuration on a length of pipe containing an insert, and a length of tracer wire.

FIG. 17 is a schematic diagram illustrating an isometric view of an embodiment a capacitive pipe insert detection instrument positioned in a closed configuration on a length of pipe containing an insert, and a length of tracer wire. In some embodiments, the instrument of FIG. 17 comprises the instrument of FIG. 14 with a sample pipe, an insert pipe, and a tracer wire. In the example shown, instrument 1701 is shown with enclosure part 1702 and enclosure part 1703 in a clamped or closed configuration around sample pipe 1721 that contains pipe insert 1723 and which is fitted with tracer wire 1722. Sample pipe 1721 and tracer wire 1722 are positioned within cutout 1719 and cutout 1720, respectively, and thus are isolated from one another.

Figure 18:
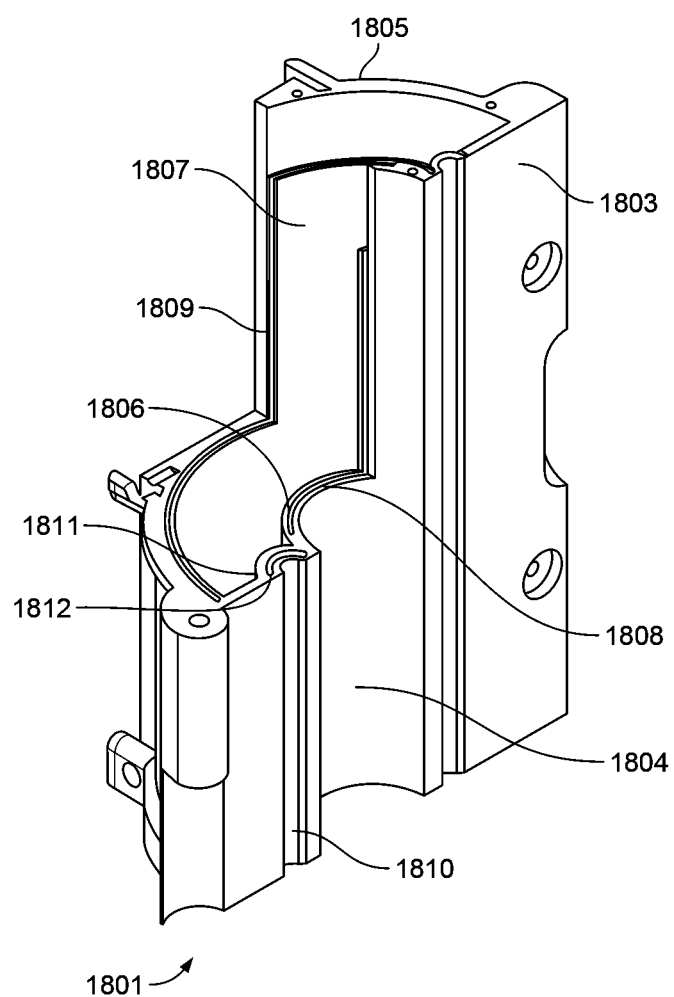
FIG. 18 is a schematic diagram illustrating a cutaway isometric view of an embodiment of part of the enclosure of a capacitive pipe insert detection instrument with slits for accommodating a transduction electrode, inner shield electrodes and an outer shield electrode.

FIG. 18 is a schematic diagram illustrating a cutaway isometric view of an embodiment of part of the enclosure of a capacitive pipe insert detection instrument with slits for accommodating a transduction electrode, inner shield electrodes and an outer shield electrode. In some embodiments, the instrument of FIG. 18 comprises a cutaway view of the instrument in FIG. 14. In the example shown, enclosure piece 1801 has inner surface 1804 and inner support wall 1806 that are separated by inner slot 1808. Enclosure piece 1801 has outer surface 1805 and outer support wall 1807 that are separated by outer slot 1809. Enclosure piece 1801 has cutout surface 1810 and cutout support wall 1811 that are separated by cutout slot 1812. In various embodiments, inner slot 1808, outer slot 1809, and cutout slot 1812 are in the range of 0.1 mm to 5 mm wide.

Figure 19:
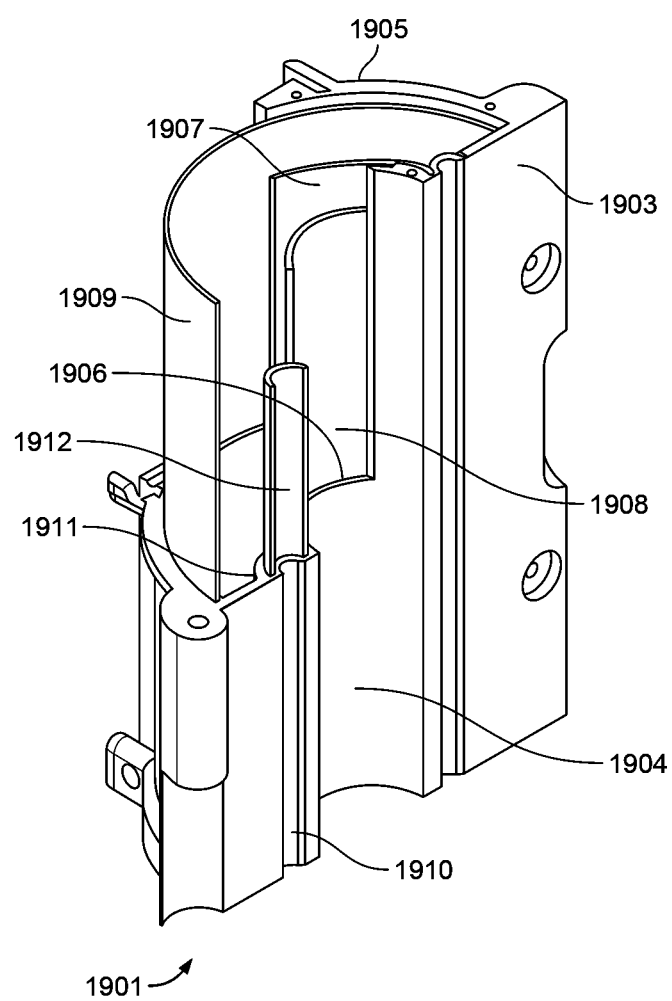
FIG. 19 is a schematic diagram illustrating cutaway isometric view of an embodiment of part of the enclosure of a capacitive pipe insert detection instrument containing a transduction electrode, inner shield electrodes and an outer shield electrode.

FIG. 19 is a schematic diagram illustrating a cutaway isometric view of an embodiment of part of the enclosure of a capacitive pipe insert detection instrument containing a transduction electrode, inner shield electrodes and an outer shield electrode. In some embodiments, the instrument of FIG. 19 comprises a cutaway view of the instrument of FIG. 14. In the example shown, enclosure piece 1901 has inner electrode 1908 positioned within an inner slot, outer electrode 1909 positioned within an outer slot, and cutout electrode 1912 positioned within a cutout slot. In some embodiments, inner electrode 1908, outer electrode 1909, and cutout electrode 1912 extend beyond their respective slots to facilitate forming electrical connections between the electrodes and other components. In some embodiments, inner electrode 1908 supports an electrostatic excitation or a voltage or current response, and outer electrode 1909 and cutout electrode 1912 are tied to electrical ground to shield against EMI. In various embodiments, inner electrode 1908, outer electrode 1909, and cutout electrode 1912 are in the range of 0.1 mm to 5 mm thick or have any other appropriate thickness. In various embodiments, inner electrode 1908, outer electrode 1909, and cutout electrode 1912 are formed using one or a combination of the following materials: copper, beryllium copper, aluminum, nickel, silver, or any other appropriate material. In various embodiments, the electrodes are attached using an adhesive or applied as a paint, paste, plating, slurry, or any other appropriate attachment method. In various embodiments in which electrodes are applied as a paint, paste, or slurry, inner electrode 1908, outer electrode 1909, and cutout electrode 1912 are applied directly to a corresponding surface of enclosure piece 1901, inner support wall 1906, outer support wall 1907, and cutout support wall 1911, and for these embodiments an inner slot, an outer slot, and cutout slot are omitted. In various embodiments, inner electrode 1908, outer electrode 1909, and cutout electrode 1912 are formed within an inner slot, and outer slot, and a cutout slot, respectively, using an overmolding process. In various embodiments, inner electrode 1908, outer electrode 1909, and cutout electrode 1912 are each connected to a connector.

Figure 20:
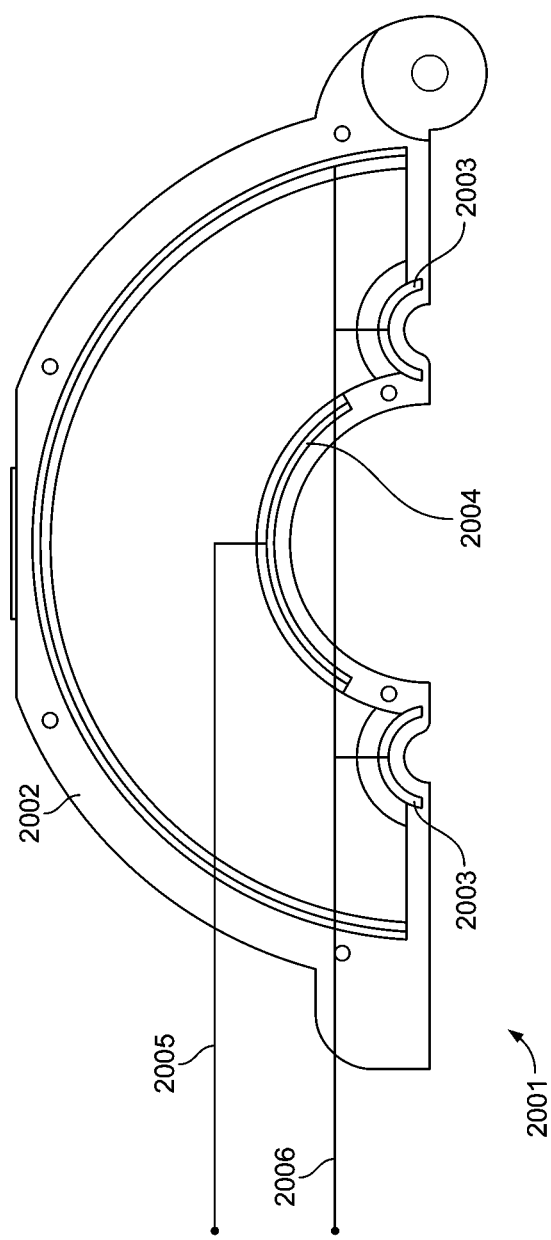
FIG. 20 is a schematic diagram illustrating an end view of an embodiment of part of the enclosure of a capacitive pipe insert detection instrument with slits for accommodating a transduction electrode, inner shield electrodes and an outer shield electrode.

FIG. 20 is a schematic diagram illustrating an end view of an embodiment of part of the enclosure of a capacitive pipe insert detection instrument with slits for accommodating a transduction electrode, inner shield electrodes and an outer shield electrode. In some embodiments, the instrument of FIG. 20 comprises an end or cross section view of a portion of the instrument in FIG. 14. In the example shown, enclosure segment 2001 has inner slot 2004 for accommodating a transduction (i.e., drive or sense) electrode, outer slot 2002 for accommodating an outer shield electrode, and cutout slots 2003 for accommodating inner shield electrodes. Shield electrodes within outer slot 2002 and cutout slots 2003 isolate a transduction electrode within inner slot 2004 from EMI originating outside the instrument and on the tracer wire, respectively. In some embodiments, a drive or sense electrode is connected to an inner conductor of a coaxial cable (represented by lead 2005) and a shield electrode is connected to the outer conductor of a coaxial cable (represented by lead 2006).

In various embodiments, a capacitive instrument for detecting inserts within non-conductive parent pipes is made to detect inserts within parent pipes sizes ranging from approximately ½ inch to 12 inches in diameter, or any other appropriate diameter. In various embodiments, a parent pipe conforms to a sizing standard such as Iron Pipe Standard (IPS), Copper Tubing Standard (CTS), or any other appropriate standard.

Concept of Operations

Figure 21:
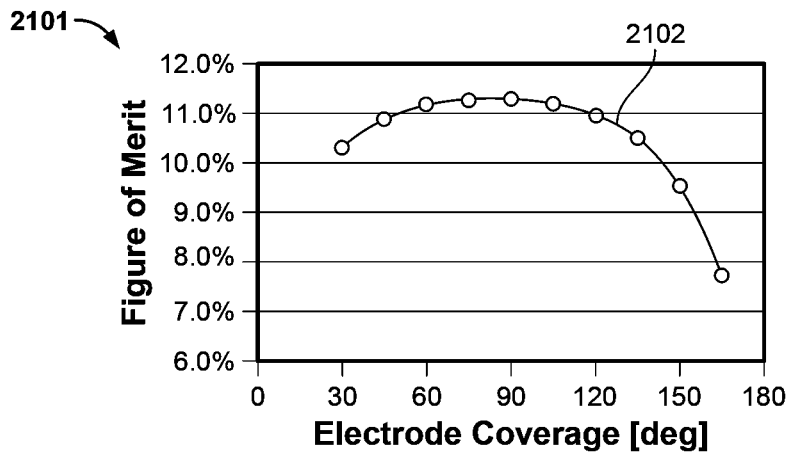
FIG. 21 is a graph illustrating a relationship between a figure of merit and the electrode angular coverage of a capacitive pipe insert detection instrument.

FIG. 21 is a graph illustrating a relationship between a figure of merit and the electrode angular coverage of a capacitive pipe insert detection instrument. In some embodiments, the graph of FIG. 21 is regarding the electrode coverage in degrees of a single electrode of a circle as viewed in cross section of the two electrode system (e.g., cross section views of FIG. 4, FIG. 5, or FIG. 6). In the example shown, the figure of merit (FOM) given by Equation 1 below is a normalized measure of the change in capacitance measured by an insert sensor caused by the presence or absence of a pipe insert. The FOM exhibits a near plateau between 75 degrees and 105 degrees with a value of approximately 11.3%. In some embodiments, it is favorable to maximize the FOM by selecting an appropriate degree of coverage of each electrode in the two electrode system.

$$FOM = \frac{C_{insert} - C_{empty}}{C_{insert} + C_{empty}} \qquad \text{Equation 1}$$

Figure 22:
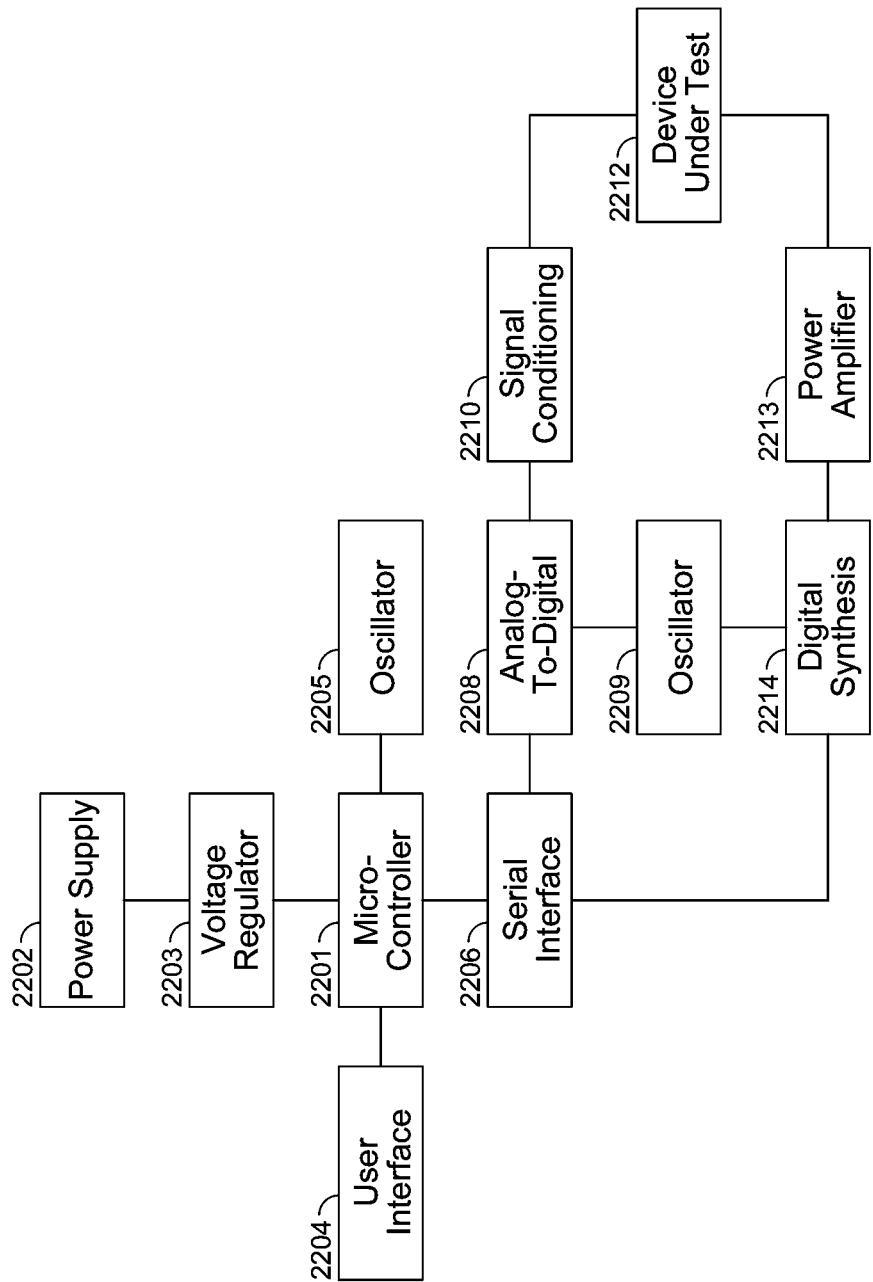
FIG. 22 is a block diagram illustrating an embodiment of the main components and sub-systems of a capacitive pipe insert detection instrument.

FIG. 22 is a block diagram illustrating an embodiment of the main components and sub-systems of a capacitive pipe insert detection instrument. In some embodiments, the instrument of FIG. 14 comprises the components and the sub-systems of FIG. 22. In the example shown, components and sub-systems of the instrument comprise microcontroller 2201, power supply 2202, voltage regulator 2203, user interface 2204, oscillator 2205, serial interface 2206, analog-to-digital converter (ADC) 2208, oscillator 2209, signal conditioning 2210, device under test (DUT) 2212, power amplifier (PA) 2213, and direct digital synthesis (DDS) module 2214. Upon power up, voltage regulator 2203 converts an electrical input from power supply 2202 into one or more stable voltages that powers micro-controller 2201 and, in some embodiments, ADC 2208, DDS 2214, signal conditioning 2210, PA 2213, any other components requiring power. In various embodiments, power supply 2202 is an onboard primary battery (e.g., lithium battery, alkaline battery, etc.) or a rechargeable battery (lithium battery, nickel cadmium battery, etc.), an external Alternating Current (AC) or Direct Current (DC) voltage, or any other appropriate power source. In some embodiments, voltage regulator 2203 provides electrical current in the range of 10 to 500 mA at one or more stable voltages in the range of 1 V to 12 V. In various embodiments, a reverse biased Zener diode is used to provide a voltage less than the voltage provided by voltage regulator 2203. Once powered up, micro-controller 2201 begins executing a program from memory. A program is used to control the user interface, data collection, and data processing functions of the capacitive pipe insert detection instrument. In various embodiments, microcontroller 2201 includes a flash memory, random access memory (RAM), read only memory (ROM), electrically erasable programmable read only memory (EEPROM), ADC, digital to analog converter (DAC), power management integrated circuits (PMIC), general purpose input output (GPIO) pins, data registers, a system clock, or any other suitable component. Oscillator 2205 provides a stable frequency reference for micro-controller 2201. In various embodiments oscillator 2205 uses a crystal (e.g., quartz, microelectromechanical system (MEMS), or any other suitable device.) or an internal complementary metal-oxide-semiconductor (CMOS) clock; a typical operating frequency for the oscillator is in the range of 1 MHz to 50 MHz. User interface 2204 translates a physical input from a user (e.g., pressing a button, actuating a switch, touching a touchpad, addressing a microphone, moving an inertial sensor, or any other suitable input) into an analog or digital input for micro-controller 2201, and translates an analog or digital output from microcontroller 2201 into a physical indication for a user (e.g., lights a light, writes text to a display, emits a sound, or provides any other suitable indication). For example, in some embodiments, user interface 2204 uses a liquid crystal display (LCD) screen to prompt the user when the instrument is ready to make a measurement, receives input from a button to initiate a measurement, and uses an LCD screen to display the measurement result to the user under the direction of a program executing on micro-controller 2201. Serial interface 2206 transfers commands back and forth between micro-controller 2201 and ADC 2208 and DAC 2214. In some embodiments, serial interface 2206 is a universal serial bus (USB), serial peripheral interface (SPI), inter-integrated circuit (I2C), RS-232, RS-485, or any other suitable interface.

In some embodiments, when instructed by micro-controller 2201 to perform a measurement (i.e., by a command from serial interface 2206), DDS module 2214 generates an excitation waveform that is amplified by PA 2213 and used to drive DUT 2212. In some embodiments, the excitation signal generated by DDS 2213 is a sinusoidal waveform with amplitude in the range of 0.1 to 10 V and frequency in the range of 1 kHz to 10 MHz and PA 2213 is an amplifier with voltage gain magnitude between 1 and 100. In some embodiments, DUT 2212 is an empty capacitive pipe insert detection instrument, an instrument clamped around an empty length of pipe, an instrument clamped around a length of pipe containing a pipe insert, or any other suitable configuration of a capacitive pipe insert detection instrument. During a measurement, signal conditioning 2210 processes an electrical response signal induced in DUT 2012 by an excitation waveform applied by DDS 2214 and PA 2213. Signal conditioning 2210 may comprise a current-to-voltage converter (e.g., a trans-impedance amplifier, a resistor, or any other suitable current-to-voltage converter), an amplifier (e.g., a low-noise amplifier, a variable gain amplifier, or some other suitable amplifier), a filter (e.g., a lowpass, bandpass, or some other suitable filter), a digital signal processor, or some other suitable signal conditioning device. A conditioned analog response signal passes from signal conditioning 2210 to ADC 2208 where it is converted into a digital word. In some embodiments, ADC 2208 has 8 to 16 bit conversion resolution and samples at 10 k to 10M samples per second. In some embodiments, oscillator 2209 provides a stable frequency reference for ADC 2208 and DDS module 2214. In various embodiments, oscillator 2209 uses a crystal (e.g., quartz, MEMS, or any other suitable device.) or an internal CMOS clock; a typical operating frequency for the oscillator is in the range of 1 MHz to 50 MHz. A digitized response signal passes from ADC 2208 to micro-controller 2201 by means of serial interface 2206. In some embodiments, a digitized response signal is processed micro-controller 2201 according to a program to determine a capacitance associated with a measured response signal and, using a library of reference capacitance values stored in memory, to infer from a capacitance whether or not a length of pipe contains a pipe insert or if a capacitive pipe insert detection instrument has a valid calibration.

In various embodiments, a memory is used to store one or more of the following: a program, calibration constants, and measurement data. In various embodiments, a Global Positioning System (GPS) receiver is provided to determine the location at which measurements are made. In various embodiments, a wired or wireless (e.g., Bluetooth, ZigBee, Wi-Fi, LTE, HSPA+, etc.) protocol is provided to relay data to an external client. In some embodiments, one or more of the components and/or sub-systems may be implemented as discrete components, part of a System-On-Chip (SOC), System-In-Package (SIP), Application-Specific Integrated Circuit (ASIC), Field-Programmable Gate Array (FPGA), etc.

Figure 23:
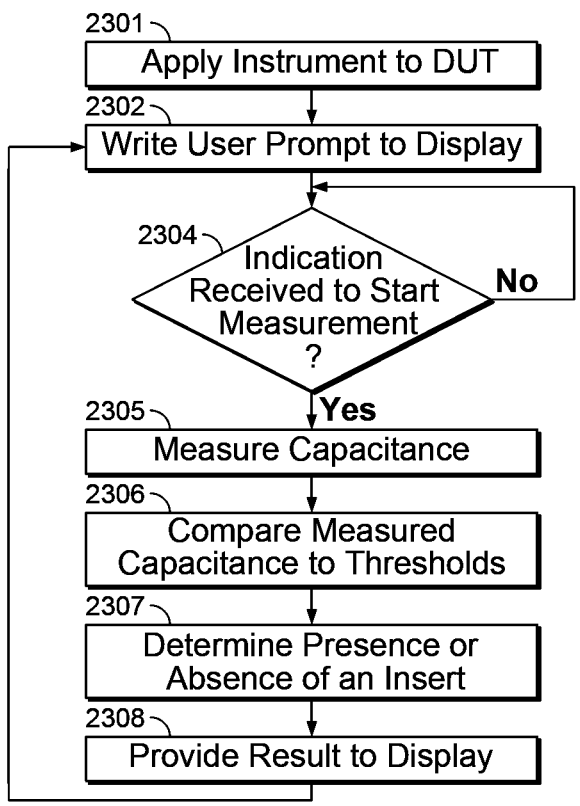
FIG. 23 is a flow diagram illustrating an embodiment of a process for determining the presence or absence of a pipe insert within a parent pipe using a capacitive pipe insert detection instrument.

FIG. 23 is a flow diagram illustrating an embodiment of a process for determining the presence or absence of a pipe insert within a parent pipe using a capacitive pipe insert detection instrument. In some embodiments, the process of FIG. 23 is executed by the instrument of FIG. 14, FIG. 15, FIG. 16, or FIG. 17. In the example shown, in 2301 the instrument is applied to the Device Under Test (DUT). For example, the instrument is positioned around the outer wall of the sample pipe and tracer wire (if applicable) by closing the enclosure parts around the sample pipe. In 2302, a user prompt is written to a display. For example, a message is displayed on an LCD display (or equivalent prompt) that prompts the user to select a measurement mode and/or begin a measurement. In 2304, it is determined whether an indication is received to start a measurement. For example, an indication of a button push (or equivalent command) is received indicating that a measurement is to be made. In the event that an indication to start the measurement is not received, control passes to 2304. In the event that an indication to start the measurement is received, then in 2305, capacitance is measured. For example, an electrostatic excitation is applied, the resulting voltage response is measured, and the corresponding capacitance of the section of sample pipe (and insert, if present) within the instrument is determined. The processor receives measurement of the capacitance. In 2306, a measured capacitance is compared to thresholds. For example, the determined capacitance value is compared to a set of previously determined threshold capacitances corresponding to a length of sample pipe not containing a pipe insert, a length of sample pipe containing a pipe insert, or another case of interest. In 2307, presence or absence of an insert is determined. For example, based on the value of the measured capacitance relative to the threshold capacitances, the presence or absence of a pipe insert within a sample pipe is determined. In 2308, result is provided to display, and control passes to 2302. For example, the measurement result (e.g., the presence or absence of an insert, a capacitance value, a temperature, etc.) is communicated to the user using an LCD display, and the program restarts. In some embodiments, another appropriate output device is used in place of or in addition to an LCD display (e.g., a light emitting diode screen, an organic light emitting diode scree, a cathode ray tube, etc.). In some embodiments, another appropriate input device is used in place of or in addition to pushbutton (e.g., a toggle, a capacitance button, a rotary dial, a touchscreen, a photodetector, etc.).

Figure 24:
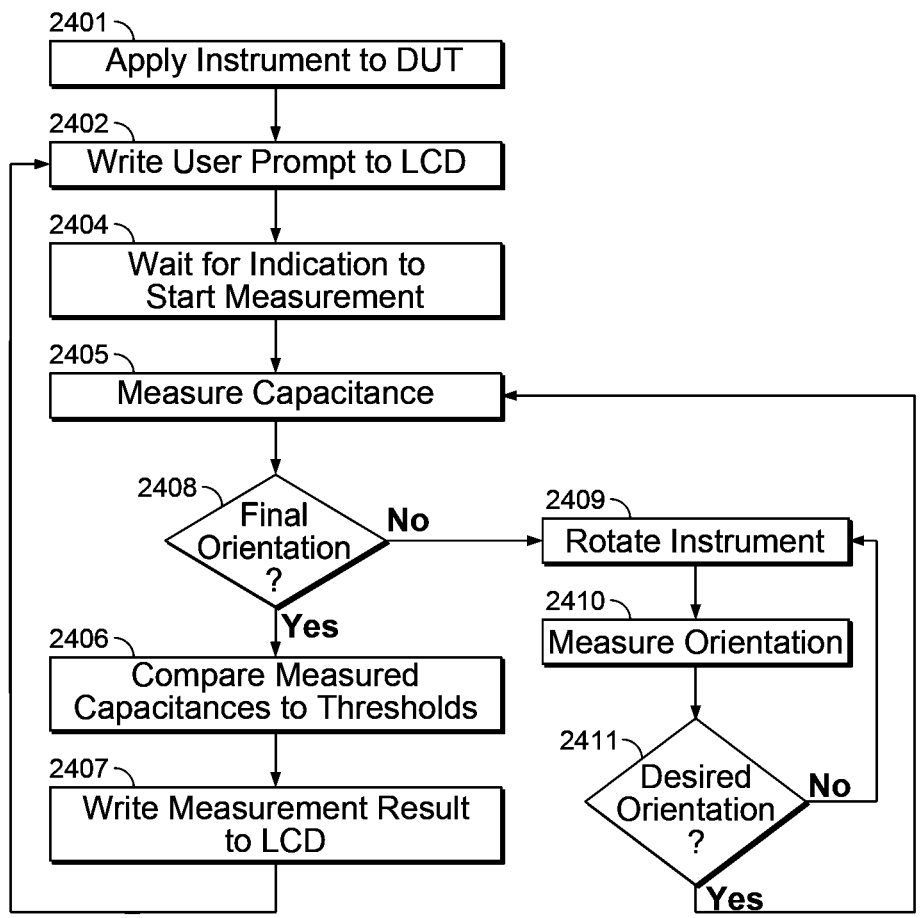
FIG. 24 is a flow diagram illustrating an embodiment of a process for determining the presence or absence of a pipe insert within a parent pipe using a capacitive pipe insert detection instrument making multiple measurements around the periphery of the parent pipe.

FIG. 24 is a flow diagram illustrating an embodiment of a process for determining the presence or absence of a pipe insert within a parent pipe using a capacitive pipe insert detection instrument making multiple measurements around the periphery of the parent pipe. In some embodiments, the process of FIG. 23 is executed by the instrument of FIG. 14, FIG. 15, FIG. 16, or FIG. 17. In the example shown, in 2401 the instrument is applied to the Device Under Test (DUT). For example, the instrument is positioned around the outer wall of the sample pipe and tracer wire (if applicable) by closing the enclosure parts around the sample pipe. In 2402, a user prompt is written to a display. For example, a message is displayed on an LCD display (or equivalent prompt) that prompts the user to select a measurement mode and/or begin a measurement. In 2404, it is determined whether an indication is received to start a measurement. For example, an indication of a button push (or equivalent command) is received indicating that a measurement is to be made. In 2405, capacitance is measured. For example, an electrostatic excitation is applied, the resulting voltage response is measured, and the corresponding capacitance of the section of sample pipe (and insert, if present) within the instrument is determined. In 2408, it is determined whether the orientation is final. For example, it is determined whether the capacitance has been measured at the final desired orientation. In the event that the orientation is final, control passes to 2406. In the event that the orientation is not final, control passes to 2409. In 2409, an indication to rotate the instrument is provided. For example, a message is provided to an LCD display that prompts the user to rotate the insert detecting instrument about the axial axis of the parent pipe. In 2410, the orientation is measured. For example, the orientation of the insert detecting instrument is determined with respect to a reference frame by using a two- or three-axis accelerometer to determine the orientation of the insert detecting instrument relative to the gravitational acceleration vector. In 2411, it is determined whether the instrument is in a desired orientation. For example, the present orientation of the instrument is compared to a desired value (e.g., one stored in a memory). In the event that the instrument is in the desired orientation, control passes to 2405. In the event that the instrument is not in the desired orientation, control passes to 2409. For example, the process loops until the measured orientation substantially corresponds to the desired one (i.e., is within +/−5%).

In the event that the orientation is final, in 2406, the measured capacitances are compared to thresholds. For example, the determined capacitance value at each orientation of the insert detecting instrument is compared to a set of previously determined threshold capacitances corresponding to a length of sample pipe not containing a pipe insert, a length of sample pipe containing a pipe insert, or another case of interest. Based on the value of the measured capacitances relative to the threshold capacitances, the presence or absence of a pipe insert within a sample pipe is determined. In 2407, the measurement result is written to a display, and control passes to 2402. For example, the result is communicated to the user using an LCD display. Basing the determination of the presence or absence of a pipe insert on capacitance measurements made at multiple orientations around the periphery of a parent pipe can decrease the likelihood of erroneous results caused by asymmetries in the pipe and/or insert. In some embodiments, another appropriate output device is used in place of or in addition to an LCD display (e.g., a light emitting diode screen, an organic light emitting diode scree, a cathode ray tube, etc.). In some embodiments, another appropriate input device is used in place of or in addition to pushbutton (e.g., a toggle, a capacitance button, a rotary dial, a touchscreen, a photodetector, etc.).

In some embodiments, the orientation Bin the cross-sectional plane of the parent pipe of the insert detecting instrument relative to the gravitational vector is calculated using Equation 2 where $a_{XL}$ and g are the measured and gravitational acceleration unit vectors, respectively, and "·" denotes the dot or scalar product operator.

$$\theta = \cos^{-1}(\vec{a}_{XL} \cdot \vec{g}) \qquad \text{Equation 2}$$

In some embodiments, electrostatic excitations for the measurement of capacitance comprise a sinusoidal excitation voltage at a frequency within a range of, for example, 1 kHz to 1 MHz with peak-to-peak amplitude in the range of, for example, 0.1 V to 10V. In some embodiments, electrostatic excitations for the measurement of capacitance comprise a series of sinusoidal excitation voltages at a set of frequencies within a range of, for example, 1 kHz to 10 MHz with peak-to-peak amplitude in the range of, for example, 0.1 V to 10V. In some embodiments, the current response resulting from each frequency in a set of electrostatic excitations is converted to a corresponding voltage response using a transimpedance amplifier. In some embodiments, multiple voltage or current responses (e.g., 2 to 1,000 responses) are averaged (e.g., using an arithmetic mean, weighted mean, etc.) to provide an average voltage or current response. In some embodiments, the complex impedance Z of a DUT is determined as a function of frequency ω from the amplitude and phase of the sets of excitation voltage amplitude and current response. In some embodiments, the capacitance of a DUT is determined using Equation 3.

$$C = \frac{1}{\omega Im\{Z\}} \qquad \text{Equation 3}$$

Figure 25:
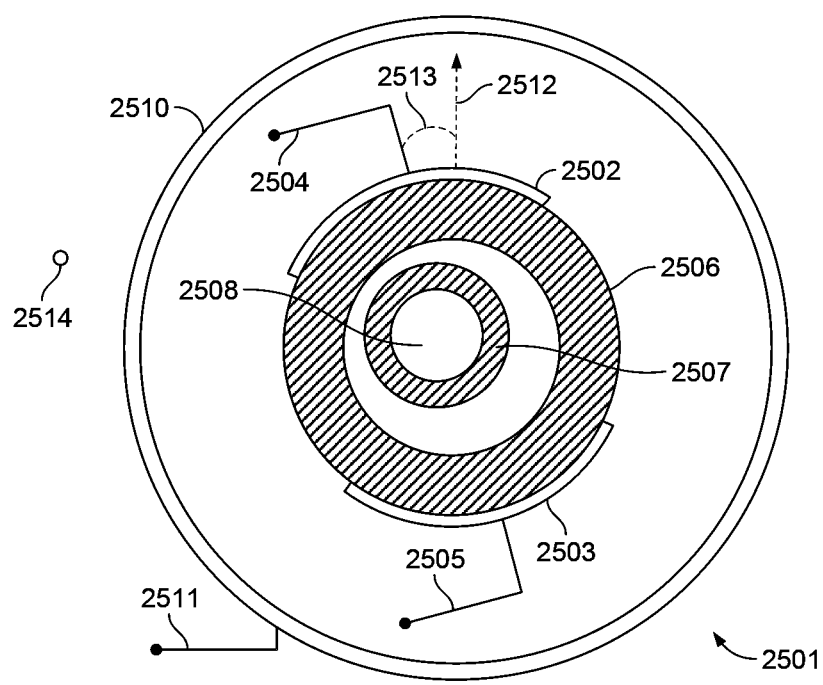
FIG. 25 is a schematic diagram illustrating a cross-sectional view of an embodiment of curved top and bottom capacitive drive and sense electrodes aligned at an angle with respect to an axis normal to a coaxial parent pipe.

FIG. 25 is a schematic diagram illustrating a cross sectional view of an embodiment of curved top and bottom capacitive drive and sense electrodes aligned at an angle with respect to an axis normal to a coaxial parent pipe. In the example shown, electrode 2502 and electrode 2503 are electrically-conductive concentric arcs in the cross section view that are positioned along the periphery of parent pipe 2506 Electrode 2502 and electrode 2503 (e.g., with respect to a line intersecting the centers of each the arcs of electrode 2502 and electrode 2503) are aligned at an angle 2513 with respect to a reference vector 2512 about an axis parallel to the axis of parent pipe 2506. Shield 2510 is an electrically-conductive concentric circle positioned around pipe 2506, electrode 2502, and electrode 2503. Tracer wire 2514 is positioned outside of shield 2510. Applying an electrostatic excitation to lead 2504 and lead 2505 creates a voltage or current response between electrode 2502 and electrode 2503, respectively, in proportion to the capacitance of parent pipe 2506 and pipe insert 2507 and each of their contents, which in turn depends on the dielectric properties of parent pipe 2506 and pipe insert 2507 and each of their contents. Thus, information about the dielectric properties of parent pipe 2506 and pipe insert 2507 can be inferred from measurements of the voltage or current response resulting from an electrostatic excitation. Shield 2510 isolates electrode 2502 and electrode 2503 from external EMI including parasitic signals on tracer 2514. In various embodiments, electrode 2502, electrode 2503, and shield 2510 are formed using an electrically conductive material including one of the following: copper, aluminum, beryllium copper, silver, or any other appropriate conductive material. In various embodiments, parent pipe 2506 is formed using a non-metallic material including one or more of the following: MDPE, HDPE, Aldyl-A, PVC, polyamide, polycarbonate, PP, PTFE, ABS, or any other appropriate non-metallic material, or a metallic material including one or more of the following: iron, steel, copper, stainless steel, or any other appropriate metallic material. In various embodiments, pipe insert 2507 is formed using a non-metallic material including one or more of the following: MDPE, HDPE, Aldyl-A, PVC, polyamide, polycarbonate, PP, PTFE, ABS, or any other appropriate non-metallic material. In various embodiments, the cylindrical volume within pipe insert 2507 contains vacuum, a liquid such as water, or a gas or combination of gasses including air, natural gas, nitrogen, methane, or any other appropriate gas and/or liquid. In various embodiments, the interstitial volume between parent pipe 2506 and pipe insert 2507 and the cylindrical volume within pipe insert 2507 each contain one or more of the following: a vacuum, a liquid such as water, or a gas or combination of gasses including air, natural gas, nitrogen, methane, or any other appropriate gas and/or liquid. In various embodiments, the annular volume between pipe 2506 and shield 2510 contains one or more of the following: a vacuum, a liquid such as water, or a gas or combination of gasses including air, natural gas, nitrogen, methane, or any other appropriate liquid and/or gas.

Figure 26:
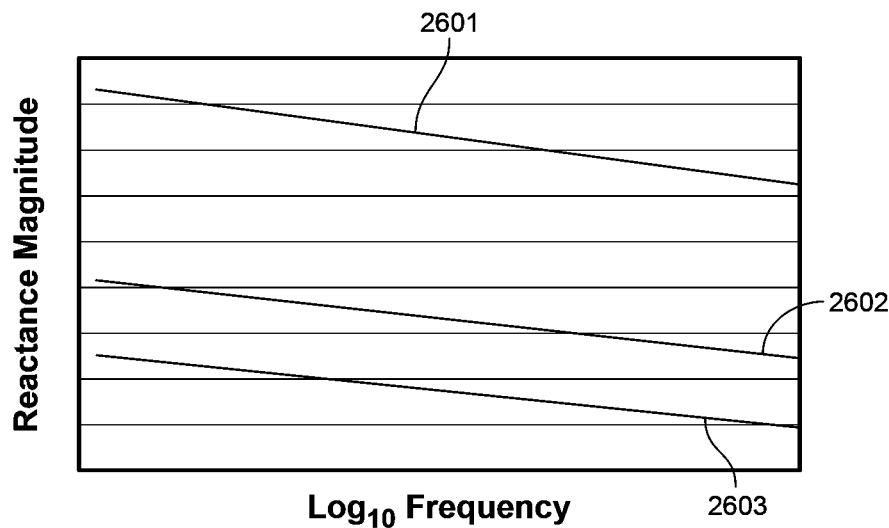
FIG. 26 is a graph illustrating a relationship between the measured impedance of a capacitive pipe insert detection instrument and the frequency of the excitation voltage waveform.

FIG. 26 is a graph illustrating an embodiment of a relationship between the measured impedance of a capacitive pipe insert detection instrument and the frequency of the excitation voltage waveform. In the example shown, response curve 2601 corresponds to the reactance (Im{Z}) measured by an empty capacitive pipe insert detection instrument in the clamped configuration. Response curve 2602 corresponds to the reactance measured by a capacitive pipe insert detection instrument clamped around a length of pipe containing no pipe insert. The presence of the pipe increases the capacitance of the system so the reactance associated with response curve 2602 decreases (for any given frequency) in relation to the reactance associated with response curve 2601 in accordance with Equation 3. Response curve 2603 corresponds to the reactance measured by a capacitive pipe insert detection instrument clamped around a length of pipe containing a pipe insert. The presence of the pipe insert increases the capacitance of the system so the reactance associated with response curve 2603 decreases (for any given frequency) in relation to the reactance associated with response curve 2602 in accordance with Equation 3. In the example shown, response curve 2601, response curve 2602 and response curve 2603 were generated by incrementing an excitation drive waveform from 90 kHz to 100 kHz in increments of 100 Hz. In some embodiments, the measured reactance is in the range of 1 k$\Omega$) to 10 M$\Omega$. Once a reactance response has been measured, a corresponding capacitance is calculated using Equation 3. In some embodiments, multiple reactance measurements are averaged together to mitigate the effect of measurement noise. In some embodiments, an arithmetic mean, least squares fit, or any other appropriate technique is used to determine a representative capacitance value for the set of capacitance values calculated from the spectrum of measured reactances.

Figure 27:
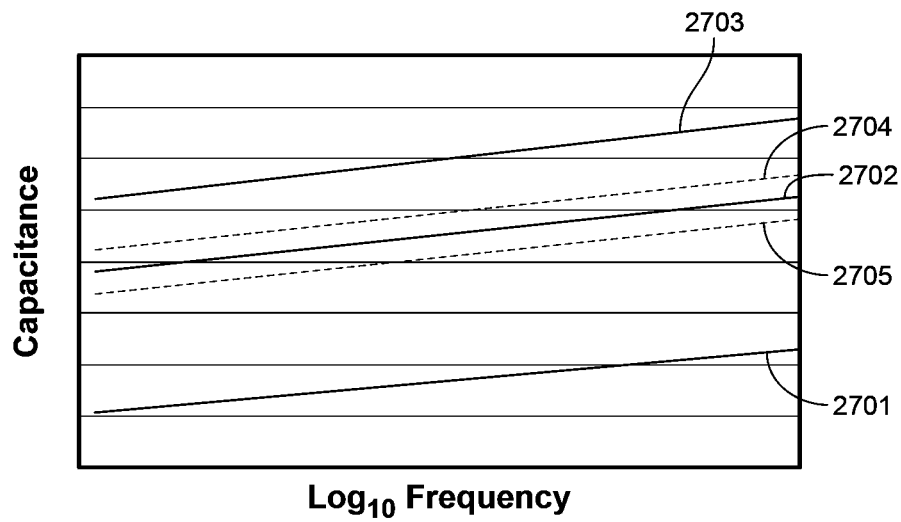
FIG. 27 is a graph illustrating a relationship between the determined capacitance of a capacitive pipe insert detection instrument and the frequency of the excitation voltage waveform.

FIG. 27 is a graph illustrating a relationship between the determined capacitance of a capacitive pipe insert detection instrument and the frequency of the excitation voltage waveform. In the example shown, response curve 2701 corresponds to the capacitance of an empty capacitive pipe insert detection instrument in the clamped configuration determined from response curve 2601 using Equation 3. Response curve 2702 corresponds to the capacitance of a capacitive pipe insert detection instrument clamped around a length of pipe containing no pipe insert determined from response curve 2602 using Equation 3. The presence of the pipe increases the capacitance associated with response curve 2702 relative to the capacitance associated with response curve 2701. Response curve 2703 corresponds to the capacitance of a capacitive pipe insert detection instrument clamped around a length of pipe containing a pipe insert determined from response curve 2603 using Equation 3. The presence of the pipe insert increases the capacitance associated with response curve 2703 relative to the capacitance associated with response curve 2702. In the example shown, curve 2704 and curve 2705 correspond to an upper threshold capacitance and lower a threshold capacitance, respectively, for determining the presence or absence of a pipe insert within a parent pipe. In some embodiments, a sample of pipe whose capacitance is determined to be less than a lower threshold capacitance associated with curve 2705 will be determined to correspond to an invalid measurement, a sample of pipe whose capacitance is determined to be greater than a lower threshold capacitance associated with curve 2705 but less than an upper threshold capacitance associated with curve 2704 will be determined to be empty (i.e., not contain a pipe insert), and a sample of pipe whose capacitance is determined to be greater than an upper threshold capacitance associated with curve 2704 will be determined to contain a pipe insert. In some embodiments, a representative capacitance value is determined for each of response curve 2701, response curve 2702, and response curve 2703 using an arithmetic mean of the capacitances $C_n$ determined for each of the $n_{freq}$ excitation frequencies. In some embodiments, the presence or absence of a pipe insert is determined by comparing the representative capacitances associated with a sample pipe and a threshold capacitance.

In some embodiments, curve 2704 and curve 2705 are linear functions or any other suitable function of the voltage excitation frequency. In some embodiments, curve 2705 is chosen to correspond to approximately 90% to 99.5% of the capacitance associated with an empty pipe at every excitation frequency and curve 2704 is chosen to correspond to approximately 100.5% to 110% of the capacitance associated with an empty pipe at every excitation frequency. In some embodiments, response curve 2701, response curve 2702, and response curve 2703 correspond to capacitances in the range of 100 fF to 1 nF or any other suitable capacitance. In some embodiments, multiple capacitance measurements are averaged together to mitigate the effect of measurement noise. In some embodiments, the number of excitation frequencies $n_{freq}$ is 1 to 100 or any other suitable number of frequencies.

Although the measuring capabilities of the instrument are described within the context of detecting solid pipe inserts in the present disclosure, it is understood that the device is equally suitable for detecting the presence of other dielectric materials within a pipe sample. For example, the device could be used to detect the presence or absence of liquid water or hydrocarbons within a sample pipe. Furthermore, whereas some embodiments of an insert sensor configured to detect the presence or absence of a pipe insert within a parent pipe may support measuring cylindrical samples, the instrument may also be used with samples having non-circular cross-sections by making appropriate changes to the enclosure and electrode geometries.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for insert detection, comprising:
   a sensor, wherein the sensor comprises electrodes with a shape to match an outer periphery of a non-metallic parent pipe, wherein the sensor is positioned surrounding the outer periphery of a non-metallic parent pipe using two enclosure halves that are connected by a hinge, wherein a half enclosure of the two enclosure halves includes a cutout electrode for surrounding a cutout space, and wherein the cutout electrode is tied to a ground to shield against signals from the cutout space; and
   a processor configured to:
      receive capacitance measurement based at least in part on a signal measured using the sensor; and
      determine presence or absence of an insert based at least in part on the capacitance measurement and a threshold, wherein the insert comprises a pipe insert located within an inner periphery of the non-metallic parent pipe.

2. The system of claim 1, wherein the sensor comprises a pair of electrodes.

3. The system of claim 1, wherein the capacitance measurement comprises providing an excitation to the sensor.

4. The system of claim 1, wherein the capacitance measurement comprises measuring a resulting voltage from the sensor.

5. The system of claim 1, wherein the capacitance measurement comprises measuring an impedance.

6. The system of claim 5, wherein the capacitance measurement comprises calculating a capacitance value using the impedance.

7. The system of claim 1, wherein determining the presence or the absence of the insert comprises comparing the capacitance measurement and the threshold.

8. The system of claim 7, wherein in the event that the capacitance measurement is below the threshold, the absence of the insert is determined.

9. The system of claim 7, wherein in the event that the capacitance measurement is above the threshold, the presence of the insert is determined.

10. The system of claim 1, wherein the capacitance measurement is one of a plurality of capacitance measurements.

11. The system of claim 10, wherein the plurality of capacitance measurements are each associated with an excitation frequency.

12. The system of claim 10, wherein an average of the plurality of capacitance measurements is calculated.

13. The system of claim 12, wherein determining the presence or the absence is based at least in part on the average.

14. The system of claim 1, wherein the threshold is one of a plurality of thresholds.

15. The system of claim 14, wherein each threshold of the plurality of thresholds is associated with a frequency.

16. The method for insert detection, comprising:
   receiving capacitance measurement based at least in part on a signal measured using a sensor, wherein the sensor comprises electrodes with a shape to match an outer periphery of a non-metallic parent pipe, wherein the sensor is positioned surrounding the outer periphery of a non-metallic parent pipe using two enclosure halves that are connected by a hinge, wherein a half enclosure of the two enclosure halves includes a cutout electrode for surrounding a cutout space, and wherein the cutout electrode is tied to a ground to shield against signals from the cutout space; and
   determining, using a processor, a presence or an absence of an insert based at least in part on the capacitance measurement and a threshold, wherein the insert comprises a pipe insert located within an inner periphery of the non-metallic parent pipe.

17. A non-transitory computer readable storage medium storing instructions that are executed by a processor to perform steps for insert detection, the steps including:
   receiving capacitance measurement based at least in part on a signal measured using a sensor, wherein the sensor comprises electrodes with a shape to match an outer periphery of a non-metallic parent pipe, wherein the sensor is positioned surrounding the outer periphery of a non-metallic parent pipe using two enclosure halves that are connected by a hinge, wherein a half enclosure of the two enclosure halves includes a cutout electrode for surrounding a cutout space, and wherein the cutout electrode is tied to a ground to shield against signals from the cutout space; and
   determining a presence or an absence of an insert based at least in part on the capacitance measurement and a threshold, wherein the insert comprises a pipe insert located within an inner periphery of the non-metallic parent pipe.

18. The system of claim 1, wherein the insert is formed using a non-metallic material.

19. The system of claim 1, wherein the cutout space has openings on both faces of the two enclosure halves to enable a tracer wire to pass through the cutout space.

* * * * *